(12) United States Patent
Zhao et al.

(10) Patent No.: US 12,004,885 B2
(45) Date of Patent: Jun. 11, 2024

(54) X-RAY TOMOGRAPHY

(71) Applicant: Xenselab, LLC, Irvine, CA (US)

(72) Inventors: Ying Zhao, Irvine, CA (US);
YongSheng Chao, Storrs, CT (US)

(73) Assignee: Xenselab, LLC, Irvine, CA (US)

( * ) Notice: Subject to any disclaimer, the term of this patent is extended or adjusted under 35 U.S.C. 154(b) by 0 days.

(21) Appl. No.: 18/067,481

(22) Filed: Dec. 16, 2022

(65) Prior Publication Data

US 2023/0363723 A1 Nov. 16, 2023

Related U.S. Application Data

(63) Continuation of application No. 17/024,467, filed on Sep. 17, 2020, now Pat. No. 11,602,315, which is a
(Continued)

(51) Int. Cl.
*A61B 6/00* (2006.01)
*A61B 6/03* (2006.01)
(Continued)

(52) U.S. Cl.
CPC ............ *A61B 6/03* (2013.01); *A61B 6/4007* (2013.01); *A61B 6/4021* (2013.01);
(Continued)

(58) Field of Classification Search
CPC ........... A61B 6/032; A61B 6/469; A61B 6/52; A61B 6/54; A61B 6/542; A61B 6/4007;
(Continued)

(56) References Cited

U.S. PATENT DOCUMENTS 4,809,308 A 2/1989 Adams et al.
5,020,086 A 5/1991 Peugeot
(Continued)

FOREIGN PATENT DOCUMENTS

EP 3129957 B1 6/2019
JP H09-322891 12/1997
(Continued)

OTHER PUBLICATIONS

Alvarez, Robert E. et al., "Energy-selective Reconstructions in X-ray Computerized Tomography," Physics in Medicine & Biology, vol. 21, No. 5, 1976, pp. 733-744.
(Continued)

*Primary Examiner* — Don K Wong
(74) *Attorney, Agent, or Firm* — Knobbe, Martens, Olson & Bear LLP

(57) ABSTRACT

An x-ray tomography system which can generate a qualitative 3D image of a region of interest using a an x-ray source, the x-ray source configured to emit x-ray radiation at the region of interest. The x-ray radiation or the x-ray source or the relative position of the x ray source configured to be moved in a two dimensional plane. An x-ray detector including a plurality of detector elements arranged in a two dimensional plane opposite the x-ray source, the x-ray detector configured to detect x-ray radiation after attenuation by the subject and provide an indication of the detected x-rays. And a processor configured to receive the indication of the detected x-rays and resolve the detected x-ray radiation into a three dimensional image. The three dimensional image is qualitative in nature.

2 Claims, 24 Drawing Sheets

Related U.S. Application Data continuation of application No. PCT/US2019/022820, filed on Mar. 18, 2019.

(60) Provisional application No. 62/729,433, filed on Sep. 11, 2018, provisional application No. 62/711,522, filed on Jul. 28, 2018, provisional application No. 62/677,312, filed on May 29, 2018, provisional application No. 62/645,163, filed on Mar. 19, 2018.

(51) Int. Cl.
| | |
|---|---|
| *A61B 6/40* | (2024.01) |
| *A61B 6/42* | (2024.01) |
| *A61B 6/46* | (2024.01) |
| *G01N 23/046* | (2018.01) |
| *G06T 11/00* | (2006.01) |

(52) U.S. Cl.
CPC .......... *A61B 6/4233* (2013.01); *A61B 6/4452* (2013.01); *A61B 6/469* (2013.01); *G01N 23/046* (2013.01); *G06T 11/005* (2013.01); *A61B 6/4035* (2013.01); *A61B 6/4078* (2013.01); *A61B 6/484* (2013.01); *G01N 2223/303* (2013.01); *G01N 2223/401* (2013.01)

(58) Field of Classification Search
CPC ... A61B 6/4028; A61B 6/4014; A61B 6/5205; A61B 6/025; A61B 6/03; A61B 6/4021; A61B 6/463; A61B 6/486; G01N 23/046; G01N 2223/204

See application file for complete search history.

(56) References Cited

U.S. PATENT DOCUMENTS

| | | | |
|---|---|---|---|
| 5,097,492 | A | 3/1992 | Baker et al. |
| 5,594,770 | A | 1/1997 | Bowles et al. |
| 5,648,997 | A | 7/1997 | Chao |
| 5,771,269 | A | 6/1998 | Chao |
| 6,173,034 | B1 | 1/2001 | Chao |
| 6,570,955 | B1 | 5/2003 | Siffert et al. |
| 6,816,564 | B2 | 11/2004 | Charles, Jr. et al. |
| 8,929,508 | B1 | 1/2015 | Alvarez |
| 9,036,879 | B2 | 5/2015 | Mendonca et al. |
| 9,579,526 | B2 | 2/2017 | Kunz et al. |
| 11,298,095 | B2 | 4/2022 | Zhao et al. |
| 11,432,786 | B2 | 9/2022 | Yamamoto |
| 11,435,421 | B2 | 9/2022 | Campagna et al. |
| 11,602,315 | B2 * | 3/2023 | Zhao ................... G06T 11/005 |
| 2004/0264628 | A1 | 12/2004 | Besson |
| 2008/0013673 | A1 | 1/2008 | Ruhmschopf |
| 2009/0022264 | A1 | 1/2009 | Zhou et al. |
| 2009/0283682 | A1 | 11/2009 | Star-Lack et al. |
| 2012/0148133 | A1 | 6/2012 | Chen et al. |
| 2013/0290030 | A1 | 10/2013 | Kay |
| 2013/0307923 | A1 | 11/2013 | Inglese et al. |
| 2014/0133729 | A1 | 5/2014 | Goshen |
| 2014/0247919 | A1 | 9/2014 | Zhang et al. |
| 2014/0270064 | A1 | 9/2014 | Oh et al. |
| 2015/0287193 | A1 | 10/2015 | Kato et al. |
| 2015/0359504 | A1 | 12/2015 | Zhou et al. |
| 2016/0095562 | A1 | 4/2016 | Baturin et al. |
| 2016/0213344 | A1 | 7/2016 | Yi et al. |
| 2018/0067061 | A1 | 3/2018 | Butani et al. |
| 2021/0137469 | A1 | 5/2021 | Zhao |
| 2021/0244374 | A1 | 8/2021 | Zhao |
| 2022/0351839 | A1 | 11/2022 | Seidnitzer et al. |
| 2023/0011644 | A1 | 1/2023 | Zhao |
| 2023/0084604 | A1 | 3/2023 | Zhao et al. |

FOREIGN PATENT DOCUMENTS

| | | |
|---|---|---|
| JP | 2009-219708 A | 10/2009 |
| JP | 2013-158444 A | 8/2013 |
| WO | WO 2009/012453 A1 | 1/2009 |
| WO | WO 2011/156526 A2 | 12/2011 |
| WO | WO 2017/144474 A1 | 8/2017 |
| WO | WO 2017/205612 A1 | 11/2017 |
| WO | WO 2019/144065 A1 | 7/2019 |
| WO | WO 2019/183002 A2 | 9/2019 |
| WO | WO 2020/028422 A1 | 2/2020 |
| WO | WO 2021/108715 A1 | 6/2021 |
| WO | WO 2022/251701 A1 | 12/2022 |

OTHER PUBLICATIONS

Gaudreault, David et al., "Comparative Study of Image Quality in Time-Correlated Single Photon Counting Computed Tomography," Journal of Latex Class Files, vol. 14, No. 8, Aug. 2015, in 7 pages.

General Electric Company, "Volume Rad (Tomosynthesis) Reference Guide," Jan. 2011, in 4 pages.

Gordon, Richard, "A Tutorial on Art." IEEE Transactions on Nuclear Science, vol. NS-21, Jun. 1974, in 16 pages.

Inscoe, Christina R., "Stationary Digital Tomosynthesis: Implementation, Characterization, and Image Processing Techniques," The University of North Carolina at Chapel Hill, ProQuest Dissertations Publishing, 2018, in 171 pages.

Invitation to Pay Additional Fees in corresponding International Patent Application No. PCT/US2019/022820, dated Jul. 9, 2019, in 12 pages.

International Search Report and Written Opinion in corresponding International Patent Application No. PCT/US2019/022820, dated Oct. 21, 2019, in 17 pages.

Mason, Jonathan H., "Quantative cone-beam CT reconstruction with polyenergetic scatter model fusion," Physics in Medicine & Biology, vol. 63, No. 22, Nov. 7, 2018.

McCollough, Cynthia H. et al., Dual- and Multi-Energy CT: Principles, Technical Approaches, and Clinical Applications, Radiology, vol. 276, No. Sep. 3, 2015, pp. 637-653.

Sisniega, A. et al. "High-fidelity artifact correction for cone-beam CT imaging of the brain," Physics in Medicine & Biology, vol. 60, published Jan. 22, 2015, pp. 1415-1439.

Speidel, Michael A., "Inverse geometry x-ray imaging: application in interventional procedures," Journal of the American College of Radiology, vol. 8, Issue 1, Jan. 1, 2011, in 8 pages.

Vedantham, Srinivasan et al., "Digital Breast Tomosynthesis: State of the Art," Radiology, vol. 277, No. 3, Dec. 2015, in 22 pages.

* cited by examiner

X-RAY TOMOGRAPHY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a continuation of U.S. patent application Ser. No. 17/024,467, filed Sep. 17, 2020, titled X-RAY TOMOGRAPHY," which claims the benefit under 35 U.S.C. § 120 and 35 U.S.C. § 365(c) as a continuation of International Application No. PCT/US2019/022820, designating the United States, with an international filing date of Mar. 18, 2019, titled "X-RAY TOMOGRAPHY," which claims the benefit of U.S. Provisional Patent Application No. 62/645,163, filed Mar. 19, 2018; U.S. Provisional Patent Application No. 62/677,312, filed May 29, 2018; U.S. Provisional Patent Application No. 62/711,522, filed Jul. 28, 2018; and U.S. Provisional Patent Application No. 62/729,433, filed Sep. 11, 2018. The entirety of each of the aforementioned applications is incorporated by reference herein.

TECHNICAL FIELD

The present disclosure relates three-dimensional x-ray imaging for medical and industrial applications.

BACKGROUND

Three-dimensional (3D) x-ray images are typically generated using computed tomography (CT), comprised of an x-ray source generating a fan beam, or point beam, and a linear or corresponding point detector or sometimes a small format 2D detector which is arc shaped. Cone Beam CT, a variation of CT, typically comprises a C-arm-mounted CT unit and a digital flat panel detector where either the subject or the source/detector rotates about an axis. Multiple images need to be taken of the entire subject in large angles, typically more than 180° to reconstruct a 3D image of the subject. This means that the subject receives a relatively high dosage of radiation. This process is also time-consuming. Present 3D CT systems are not suitable for portability, especially outside of hospitals or surgical centers or mobile diagnostics and surgical stations.

Presently non-rotating tomography is typically achieved by using one or more 2D flat panel detector(s) combined with two or more x ray sources on a linear array or an arc array or a 2D plane or 3D space.

Inverse geometry CT tomography-based techniques requires the use of a two-dimensional (2D) collimator with holes combined with a scanning x-ray source that emits through these holes before passing through the subject.

The resultant tomography images in non-rotation CT systems are not high resolution and cannot offer quantitative information generally provided by a 3D CT scanner.

Scatter interference is a major issue in both rotational and non-rotational CT.

In rotational CT, Scatter to primary x ray Ratio (SPR) scales almost proportional to the rotating axis angle coverage of the X ray cone beam. However, with lower rotation axis coverage, longer scanning times are required for images acquisition needed for tomography.

Currently, major efforts are spent on new concepts for Spectral CT, which uses the spectral information of transmitted X-rays to extract additional information about the scanned patient or object. SPR is high in Spectral CT. For lower energies, the primary intensity is increasingly covered by scattered radiation. For the constraint that the scatter-to-primary ratio is recommended to not exceed a value of one, the measured energies of single photons are recommended to be employed for spectral processing above a certain limit, for example, approximately between 30-35 KeV.

In CT, with increasing scatter to primary ratio (SPR, image artifacts emerge and degradation in image quality.

Anti Scatter Grid (ASG) is a key solution for reducing scatter in CT. Even with ASG corrections, the SPR remain to be for example, 20% or much more for many energy levels.

For high resolution imaging, Contrast to Noise Ratio, CNR an indicator for image quality, may not improve significantly and the visibility of low contrast details may be reduced with ASG.

SUMMARY

Most current CT reconstruction theory assumes that X-ray photons are absorbed or pass through the subject illuminated without interaction, meaning when SPR is 0. In human body imaging, the ratio of scatter to the primary signal is generally as high as between 50% and 100%. The present disclosure provides a system which can generate a complete 3D image of a region of interest from a two dimensional scanning process. The generated image can have a thickness or depth, or dimension (for example, in a z axis plane) comprising three or more datapoints. Each data point can be resolvable by x-ray measurement or optical measurements or other dimensional measurement methods. This can be done by minimizing the number of measurements using a 2D detector. This can be done by minimizing introduction of unknowns pixels outside of the region of interest in 1D, 2D and 3D space. Minimizing the introduction of unknowns can be done by minimizing the movement distances and movement dimensions, by minimizing hardware and movement complexity, by minimizing x-ray acquisition time, by minimizing radiation exposure and/or by simplification of 3D x-ray imaging method and apparatus of prior art.

By using a compact system with a small number or no moving parts, this disclosure provides a three dimensional x-ray imaging system using a two dimensional system. The system can also generate x ray measurements for a region of interest of a subject with multiple components internally, which can be analyzed quantitatively including material decomposition, identification and characterization and determination measurements of physical and chemical characteristics of the components, such as atomic weight, density, detailed dimensions and microstructures and features in space, localization of components in space, dynamic movements characteristics, fluid dynamics, temporal marker identification and localization, flexibility of the components, interaction between components, such as molecular and/or cellular interactions, identification of a component based on one of more such characteristics. The system can provide all of the above benefits in one system. This type of system has wide application in hospitals, surgical centers, and mobile stations. It also provides portability of such a system in conventional portable formats, carry-on, foldable for field applications such as sports medicine, veterinary, remote and ambulatory diagnostics and imaging guidance and material identification in the field. The present disclosure can also provide ultrafast image construction of 3D images to enable real time measurement and time dependent measurements in multiple dimensional imaging.

The present disclosure can also enable quantitative imaging for other non-rotational tomography systems to have more capabilities, for example Inverse Geometry Scanning fluoroscope, multiple dimensional system using 2D detectors coupled with motorized x-ray sources which can move in an arc or linearly, and/or static multiple x-ray sources, systems with X ray source(s) can place or move in 1D, 2D or 3D dimensions, pixelated 2D flat panel x-ray sources, or an x ray source comprised of a cathode, each having a plurality of individually programmable electron emitting units for emitting an electron beam when an electric field is applied, an anode target that emits X-ray beam when subjected to collision of the electron beams emitted an X-ray source, and/or metal liquid jet sources.

The present disclosure improves imaging modalities such as x ray microscopes and interferometry including Fourier transform methods, x-ray interferometry, coherence x-ray phase contrast x ray imaging, coherence contrast x-ray imaging, by providing a fast and non-rotational CT system and in some cases, providing quantitative capabilities.

The speed bottle neck in acquiring fast 3D images in the prior art is generally the speed of the motion system, compared to the present disclosure, the speed limiting factor is the frame rate of the detector.

Objects of the present disclosure will become apparent in light of the following drawings and detailed description of the disclosure.

BRIEF DESCRIPTION OF THE DRAWINGS

For a fuller understanding of the nature and object of the present disclosure, reference is made to the accompanying drawings, wherein.

DETAILED DESCRIPTION

A generalized spectral imaging description is described in Handbook of Medical Imaging by J. T. Dobbins III, Image Quality Metrics for digital systems, 2000, pp 161-219, a projected signal from a detector element, at energy level $\Omega$ $$\in \{E1, E2, E3 \ldots\}$$

$$D(\Omega) = q\Omega \int \Phi \Omega(E) \exp[-\mu 1(E)t1 - \mu 2(E)t2 - \mu 3(E)t3 \ldots] \times S\Omega(E) dE, \quad (1)$$

where q is the number of incident photons, $\Phi$ is the normalized incident energy spectrum, and S is the detector response function. Linear attenuation coefficients and integrated thicknesses for a number of materials that make up the object are denoted $\mu$ and t, which attenuate the X ray beam according to Lambert-Beers law. If we define attenuation of the subject along a projected path in a measurement unit $\mu(E)t$ where t=time of a measurement unit, then when the measurement unit is a pixel pitch, $\mu(E)t$ is then the attenuation from a pixel, named as X. If there are p pixels along the projected path measured by a detector element, the equation can be rewritten as $$D(\Omega) = q\Omega \int \Phi \Omega(E) \exp[-X_1 - X_2 - X_3 \ldots -X_z] \times S\Omega(E) dE, \quad (2)$$

Figure 30:
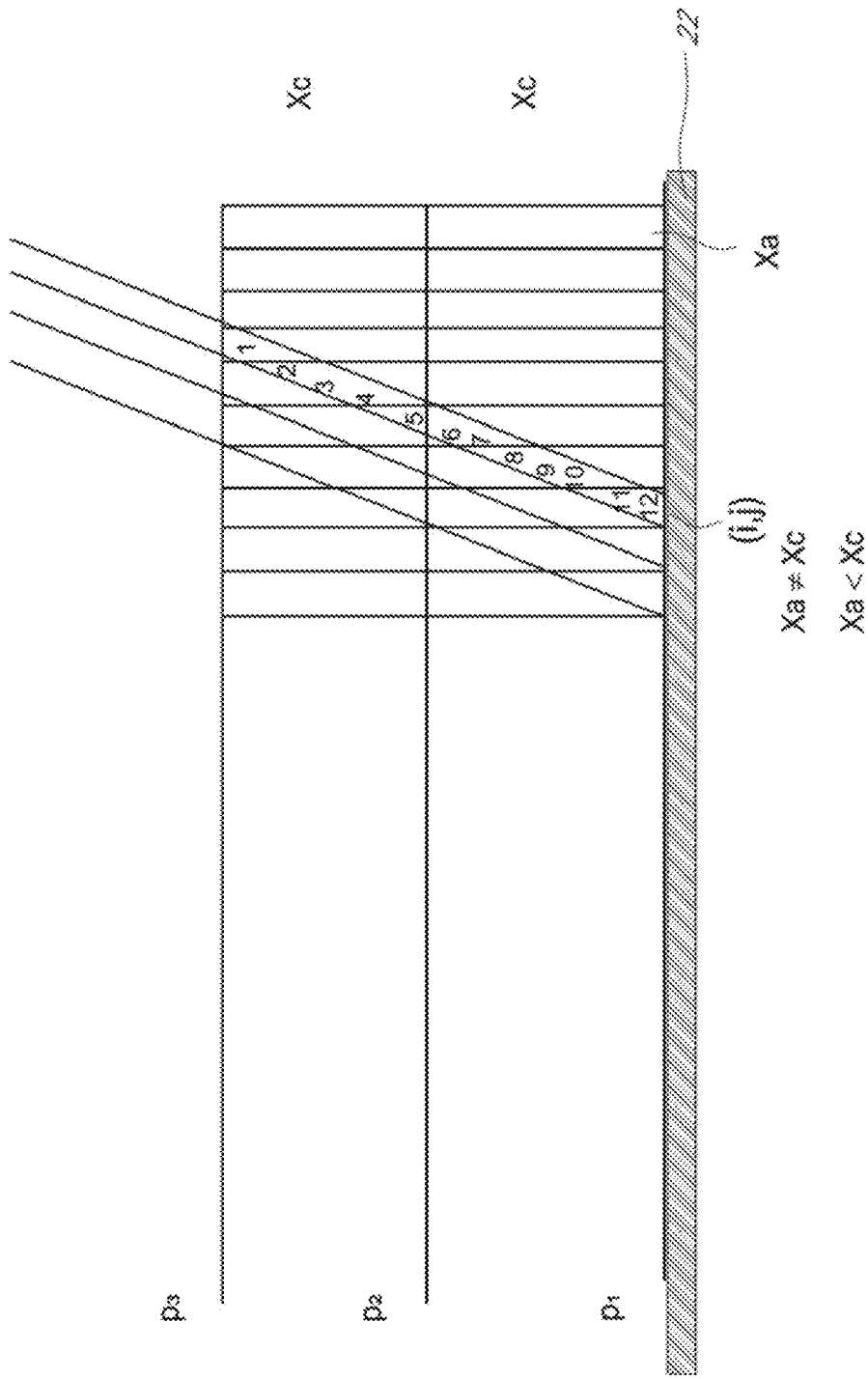
FIG. 30 illustrates a number of pixels along a projected path.

For example, as illustrated in FIG. 30, z=12.

The basic method is to solve linear equation system(s) with m×n×p variables, and m×n×p equations. Current CT methods assume that the pixel has a size Xa=Xb=Xc, we will extend to the case where Xc is not equal to Xc. When looking at the x ray passing the pixels, current methods, take the value 1 or 0, 1 for the ray passing through the pixel, 0 if not. When passing through the volume will always the same. In the present disclosure, before conducting acquisition, a registration is made at each angle and x ray emitting position. (I,j) receives signal passing through 1, 2, . . . 12, each subpixel transmission can be calculated. Assuming that inside each pixel, the transmission is uniform and proportion to the volume.

The present disclosure includes methods and systems for producing three-dimensional (3D) images of a subject using two-dimensional (2D) x-ray detectors, by removing scatter, by a calibration method and a new 3D reconstruction method. The methods and systems can include execution a number of steps, some of which are optional, as described below: (1) calibration, (2) acquiring 2D images from at least two different x-ray source locations relative to the subject, (3) processing the 2D images to separate primary x-rays from scatter, (4) functional processing of the 2D images, (5) processing to produce 3D images from the 2D images, functional processing of the 3D images, and/or presentation of the acquired information.

Figure 1:
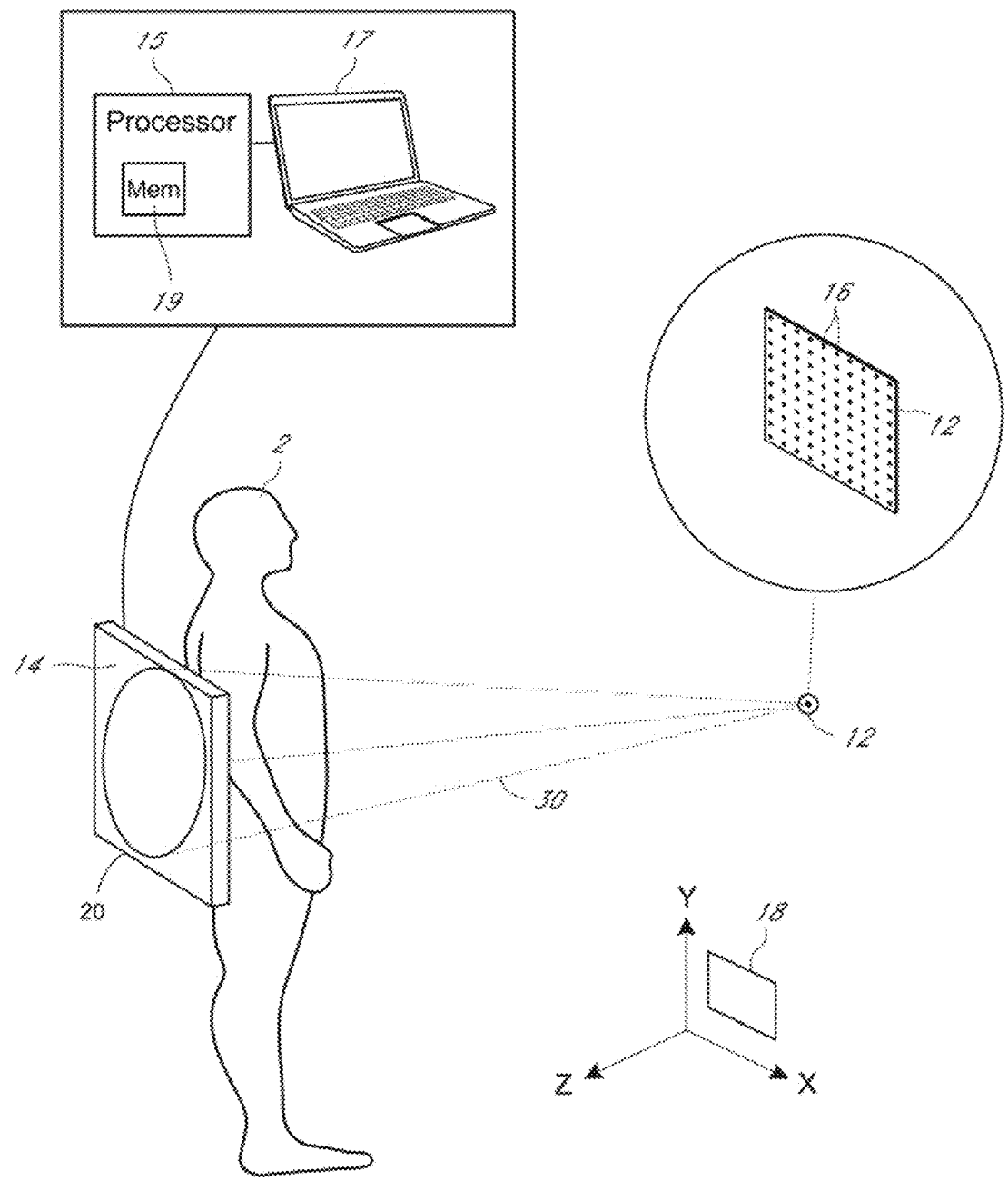
FIG. 1 is a schematic diagram of the basic hardware configuration for use by the present disclosure.

The preferred basic hardware employed by the present disclosure is shown schematically in FIG. 1. It includes an x-ray source 12 and a two-dimensional (2D) x-ray detector assembly 14. The image subject 2 is positioned between the source 12 and detector assembly 14. The detector assembly 14 communicates with a processor 15, including memory 19. The processor communicates with user input and outputs 17, including, for example, a display screen, keyboard and or mouse as would be understood by a person of skill in the art. Other user interface elements can also be used as would be understood by a person of skill in the art from the present disclosure.

As mentioned in step (2) above, a number of 2D images are acquired. For each image, the location 16 from which the x-rays 30 are emitted relative to the subject 2 is moved in a plane 18 parallel to the plane of the detector assembly 14. Consequently, the x-ray source 12 includes mechanisms for such motion, as described in detail below. The location from which the x-rays 30 are emitted is referred to as the emitting location 16 in the remainder of the present specification.

As mentioned in step (3) above, primary x-rays and x-ray scatter are separated in the 2D images prior to using the images. Typically, scatter is removed and discarded, which is why the separation is generally referred to as scatter removal in the remainder of the present specification. In some cases, however, scatter is used separately in, for example, trans vascular imaging, material differentiation, and identification and inspection for better visualization of low atomic z tissues.

Primary X-Ray and Scatter Separation Methods

Figure 2:
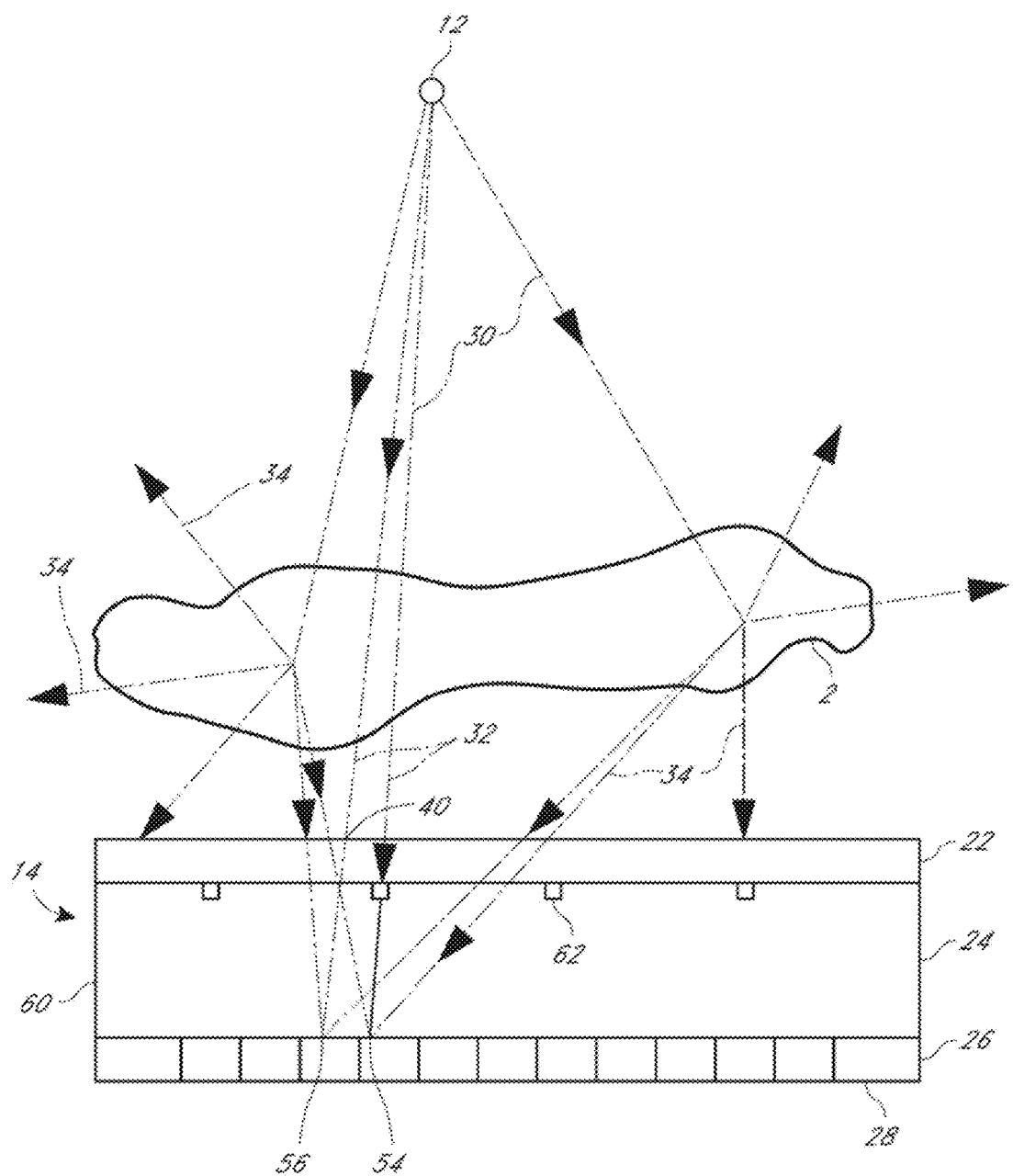
FIG. 2 is a schematic diagram of the hardware configuration of FIG. 1 with a three-layer detector structure wherein the beam selector with a fixed focal point blocks primary x-rays from selected locations of the rear detector.

With reference to FIG. 2, when x-rays 30 from the source 12 impact on the subject 2, a portion of the x-rays 30 passes through the subject 2 directly to the detector assembly 14 without a change in the direction of propagation. These are called primary x-rays 32 and convey true information about the attenuation properties of subject 2. The remainder of the x-rays 30 are randomly scattered as a result of interactions with the material of the subject 2. These are called scatter 34 and distort the true information. In some cases, such distortion is used for forming separated images which can be useful in representing true information about the subject as well.

Under some circumstances, scatter can be ignored. For example, where the detector assembly 14 is a single 2D detector 20 that will receive both primary x-rays 32 and scatter 34, it can be assumed that scatter 34 is present but in a sufficiently small amount that qualitatively correct, yet quantitatively inaccurate, imaging results can still be obtained under certain circumstances. To what extent the amount of scatter 34 is acceptable is case-dependent and must be determined by a case-specific analysis.

Primary x-rays and x-ray scatter can also be separated in the time domain where a fast x-ray source is used. This method employs the characteristic that primary x-rays 32 travel in a straight line from the source 12 to the detector assembly 14, taking the least amount of time in transit. Because scatter 34 does not travel in a straight line from the source 12 to the detector assembly 14, it takes a longer time to reach the detector assembly 14. Consequently, x-rays reach any given detector cell 28 continuously over a period of time, where only the first x-rays are the primary x-rays. All others are scatter. Unfortunately, x-ray generation that allows for this time of analysis is extremely expensive and not practical.

Apparatus and methods described in the Chao's disclosure in U.S. Pat. Nos. 6,052,433A, 5,648,997A, 5,771,269A, 6,173,034B1, 6,134,297A may be used in scatter removal with any embodiment of the present disclosure including examples where x ray source emitting positions are close together enough that the use of beam selecting means are not affected essentially. The foregoing disclosures are incorporated herein by reference in their entirety.

In one example of this method, the source 12 is capable of generating x-rays in extremely short pulses, for example, on the order of a picosecond in duration, and the detector assembly 14 is a 2D detector 20 capable of extremely fast image capture, on the order of a picosecond. The captured image includes at least the primary x-rays 32 and the scatter 34 that reaches the detector 20 during the capture time window. If the capture window is short enough, the amount of scatter 34 in the captured image is minimized. As the capture window becomes shorter, scatter 34 becomes a smaller component of the captured image.

Another method is separation of primary x-rays 32 and scatter 34 in the frequency domain. It employs the characteristic of some materials wherein the x-rays are modulated in space when passing through the material by attenuation. The x-rays 30 from the x-ray source 12 are modulated with a different, typically much higher, frequency than that of scattered x-rays from the subject 2. The high-frequency attenuation-modulated x-rays, which are the primary x-rays, and the scattered x-rays, can be separated by post-image processing.

The present disclosure contemplates that any form of x-ray modulator can be used. One example is a high-spatial-frequency pattern board consisting of attenuating blockers.

In another example, to separate x-ray signals by primary x-rays and scatter, in the spatial, frequency, or time domain, the modulator is a phase retarder, diffractive grating beam splitter with high-spatial-frequency pattern. In one form, such a modulator is comprised of crystals or x-ray optics such as beam splitters, for example, a kinoform structure. Additionally, such materials can be modulated or tunable by acoustic waves in at least one dimension. In another example, the modulator is a MEM device, which operates as a high-spatial-frequency pattern board consisting of attenuating blockers, phase modulators, or polarity modulators. Such modulator can operate in a static or tunable state depending on the application.

Another example is that an interferogram is generated by applying modulation in space, time, or frequency, or combinations of two or more domains, so that primary x-rays and scatter are separated based on the difference in frequency, or time or spatial location.

In another mechanism, x-ray beams from two or more x-ray sources are combined using a transmissive beam combiner. The interference fringes of x-ray sources at an energy level or at a specific wavelength of x-ray moves as the phase difference between x-ray beams of the x-ray sources change relative to each other or alternatively as the wavelength of the x-ray changes. The result is the modulated interferogram creating a modulated spatial pattern, which can be separated from that of scattered x-rays.

Similarly, one or more gratings are used to produce two or more minisources of the x-ray source 12. The grating can be a dynamic or tunable grating, such as those formed as MEMs, or they can be static, such as a crystal grating. X-ray beams from the minisources interfere with each other and as the grating is tuned, a moving interference fringe pattern is created. The result is the modulated interferogram creates a modulated spatial pattern.

Similarly, a grating or a beam splitter can be used to split at least one x-ray source 12 into two or more minisources with variable phases. As the wavelength or energy of the x-ray changes, the interference pattern moves in space. The scatter and the primary x-rays are separated as the scattered x-ray are separated from the signals which result in the interference pattern measurements.

Another method of scatter and primary x-ray separation is described in detail in U.S. Pat. No. 6,134,297. The detector assembly 14 is a three-layer structure of a front 2D detector 22 closest to the source 12, a 2D beam selector 24, and a rear 2D detector 26, as shown in FIG. 2. The combination of primary x-rays 32 and scatter 34 reach and pass through the front detector 22. The beam selector 24 allows only scatter 34 through to selected locations 54 of the rear detector 26.

The beam selector 24 can be an array of cylindrical shapes 62 comprises x-ray-absorbent material and supported by a thin plastic sheet 60 having negligible x-ray absorption. The cylinders 62 are fabricated such that their axes are aligned with the travel direction of the primary x-rays 32. As a result, the cylinders 62, within their cross-sectional areas, block all x-rays coming directly from the x-ray source 12. Thus, each cylinder 62 produces a selected "shadowed" location 54 on the rear x-ray detector 26 where the strength of the primary x-rays 32 is essentially zero, while the strength of the scatter 34 is essentially unaffected.

Because the cylinders 62 have a finite size, a small portion of scatter 34 will not reach the shadowed locations 54. However, as long as the cylinders 62 are small, this scatter 34 can be controlled to be negligibly small. If the cylinders 62 are too large or there are too many, too much scatter 34 would be prevented from reaching the rear detector 26. The more cylinders 62 there are in the beam selector 24, the greater the accuracy of the measurement at the rear detector 26.

The cylinders 62 are fabricated such that their axes are aligned with the direction of the travel of the primary x-rays 32, which means that the cylinders 62 are not parallel to each other, but are radial to the x-ray source 12.

The material of the cylinder 62 must ensure that substantially all primary x-rays 32 are absorbed and, further, that it does not produce any secondary x-ray emission or cause any additional scattering. To meet these requirements, chemical elements with a medium atomic number Z are preferred, for example, materials with Z between 20 and 34. The cylinders 62 can also have a multilayer structure, with a high-Z material in the core and a medium-Z material outside. The high-Z material absorbs x-rays most efficiently and any secondary x-ray emissions from the core material are efficiently absorbed by the outside layer without inducing further secondary emissions.

The thickness or the height of the cylinders 62 is dependent upon the x-ray energy, where higher energy requires thicker cylinders. In lower energy x-ray imaging, for example, in mammography, the cylinders 62 can be thin disks.

The above-described detector assembly 14 is used to remove scatter 34 from the image as follows. A low-resolution scatter image is read from the selected locations 54 of the rear detector 26. A low-resolution composite image is read from chosen locations 56 of the rear detector 26 that receive both primary x-rays 32 and scatter 34 and that uniformly cover the entire image plane of the rear detector 26 and are close to the selected locations 54. The scatter-only image is extended to the chosen locations 56 by interpolation. The interpolation does not cause significant error because of the physical nature of the scatter 34. As long as there are a sufficiently large number of data points, the error incurred due to interpolation is negligible in comparison with other error sources, such as statistical fluctuations of x-ray photon numbers.

The scatter-only interpolated image is subtracted from the low-resolution rear composite image to produce a low-resolution primary x-ray image at the chosen locations 56. A low-resolution primary x-ray front detector image is calculated from the front detector locations 40 aligned with the chosen rear detector locations 56. A low-resolution scatter image is determined by subtracting the low-resolution primary x-ray rear detector image from the low-resolution front detector composite image. A high-resolution scatter image is calculated by interpolating the low-resolution scatter image. The high-resolution scatter image is subtracted from the high-resolution composite image to produce a high-resolution primary x-ray image.

The above-described beam selector 24 must remain fixed relative to the emitting location 16 such as illustrated in FIG. 1 because the cylinders 62 must remain aligned with the source x-rays 30 from the emitting location 16 to work properly. The detectors 22, 26 do not have to move, but will need to move if the beam selector 24 is fixed to the detectors 22, 26. If the emitting location 16 moves a small enough distance that the cylinders 62 are sufficiently aligned with the source x-rays 30, then the beam selector 24 does not have to move.

Figure 3:
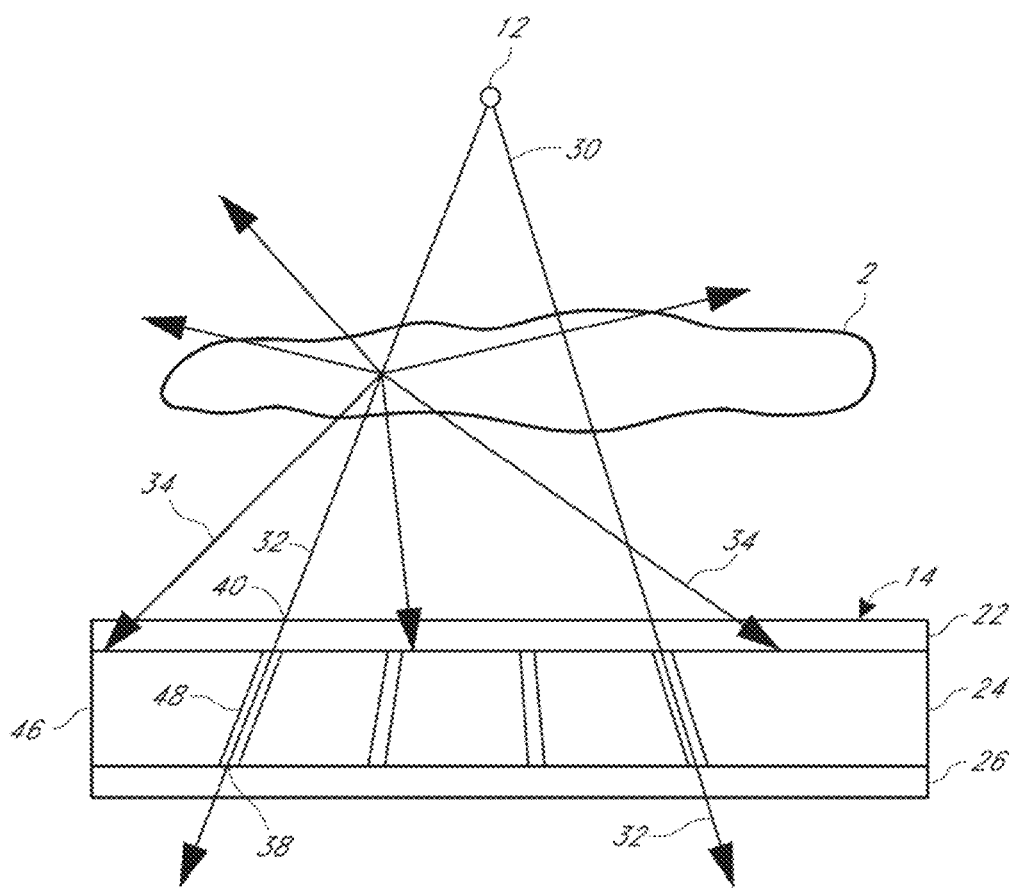
FIG. 3 is a schematic diagram of the hardware configuration of FIG. 1 with a three-layer detector structure wherein the beam selector with a fixed focal point blocks scatter from selected locations of the rear detector.

Another method of scatter removal is described in detail in U.S. Pat. Nos. 5,648,997 and 5,771,269. The detector assembly 14 is a three-layer structure of a front 2D detector 22 closest to the source 12, a 2D beam selector 24, and a rear 2D detector 26, as shown in FIG. 3. The combination of primary x-rays 32 and scatter 34 reach and pass through the front detector 22. The beam selector 24 allows only primary x-rays 32 through to selected locations 38 of the rear detector 26.

In the simplest configuration, the beam selector 24 is a sheet 46 of x-ray-absorbent material having a large number of straight through-holes 48. The holes 48 are fabricated such that their axes are aligned with the travel direction of the primary x-rays 32, which means that, because the x-rays are emitted from essentially a point source, the holes 48 are not parallel to each other, but are radially aligned to the x-ray source 12.

Because of this alignment, the holes 48 permit all x-rays traveling along the axes of the holes 48 to pass through, while almost all x-rays traveling in directions deviating slightly from the hole axes are completely absorbed by the bulk material of the beam selector 24. Thus, only the primary x-rays 32 reach the rear detector 26. Because the holes 48 will always have a finite size, a small portion of scatter 34 will reach the rear detector 26. However, as long as the hole size 48 is small and the thickness of the beam selector 24 is sufficiently large, this portion of scatter 34 can be controlled to be negligibly small in comparison with other sources of error.

Preferably, the holes 48 are as small as practical. If the holes 48 are too large, they will not prevent enough of the scatter 34 from reaching the rear detector 26. Preferably, there are as many holes as practical in the beam selector 24. The more holes 48 there are, the greater the accuracy of the measurement at the rear detector 26.

The material of the beam selector 24 must ensure that all scatter 34 is absorbed and that, except for the primary x-rays 32 passing through the holes 48, none of the other radiations, including scatter 34 and secondary emissions caused either by primary x-rays 32 or by scatter 34, reach the rear detector 26.

The above-described detector assembly 14 is used to remove scatter 34 from the image as follows. A low-resolution primary x-ray image is read from the selected locations 38 of the rear detector 26. A high-resolution composite (primary x-rays 32 and scatter 34) image is read from the front detector 22. A low-resolution front detector composite image is either read from or calculated from the front detector locations 40 aligned with the selected rear detector locations 38. A low-resolution front detector scatter image is determined by subtracting the low-resolution rear detector primary x-ray image from the low-resolution front detector composite image. A high-resolution front detector scatter image is calculated by interpolating the low-resolution front detector scatter image. The high-resolution front detector scatter image is subtracted from the high-resolution front detector composite image to produce a high-resolution primary x-ray image.

Because only the selected locations 38 on the rear detector 26 are used, an alternative structure for the rear detector 26 is to place one or more detector cells at the base of each hole 48 rather than using an entire 2D detector with most of it unused.

The above-described beam selector 24 must remain fixed relative to the emitting location 16 because the holes 48 must remain aligned with the source x-rays 30 from the emitting location 16 to work properly. The detectors 22, 26 do not have to move, but will need to move if the beam selector 24 is fixed to the detectors 22, 26. If the emitting location 16 moves a small enough distance that the holes 48 are sufficiently aligned with the source x-rays 30, then the beam selector 24 does not have to move.

If there are only a very small number of emitting locations 16, the beam selector 24 can have a set of holes 48 with a different focal point for each of the emitting locations 16. The holes 48 for the different sets have different selected locations 38 so that scatter 34 resulting from one source location does not affect the signal from the other source locations. This configuration of beam selector 24 does not have to move with the emitting location 16.

The following beam selectors 24 have adjustable focal points so that the beam selector 24 does not have to move as the emitting location 16 moves.

Figure 4:
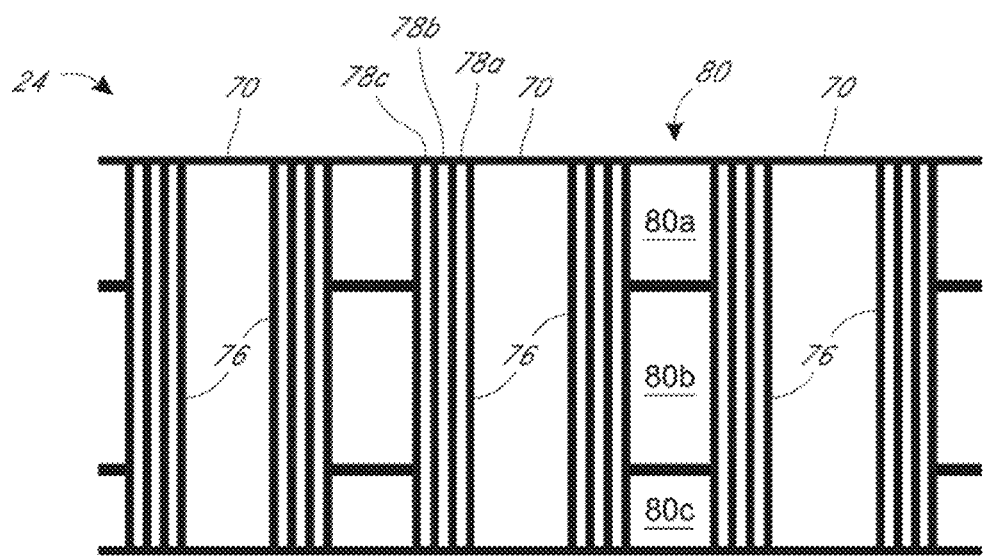
FIG. 4 is a side view of a portion of a beam selector with an adjustable focal point using compressible materials that blocks scatter from selected locations of the rear detector.

The beam selector 24 of FIG. 4 comprises x-ray-absorbent material(s) with a large number of straight through-holes 70. Each hole 70 is formed by a rigid, hollow tube 76 made of one or more x-ray-absorbent materials in layers 78 with different x-ray-energy absorbing characteristics. In FIG. 4, the tubes 76 can comprise three layers 78a, 78b, 78c of different x-ray-absorbent materials. Multiple x-ray-absorbent materials provide efficient absorption for multiple-energy systems or for single-energy systems where the energy is spread over a wide range, for example 15 KeV to 500 KeV. Possible materials include tungsten (W), tin (Sn), and copper (Cu). When the materials are selected to absorb most efficiently at different energy levels, the thickness of the tube wall 78 can be minimized.

The region 80 between the tubes 76 comprises a compressible, x-ray-absorbent material, for example, an elastomer mixed with an x-ray-absorbent material. As with the tube walls 78, the region 80 can comprise multiple layers with different x-ray-energy absorbing characteristics. In FIG. 4, the region 80 comprises three layers 80a, 80b, 80c of different x-ray-absorbent materials, for example, an elastomer mixed with tungsten 80a, an elastomer mixed with tin 80b, and an elastomer mixed with copper 80c. The ratio of elastomer to x-ray-absorbent material must be chosen such that the compression characteristics of the elastomer and the absorbing ability of the x-ray-absorbent material are maintained. Typically, the ratio of elastomer to x-ray-absorbent material is in the range of from 1:1 to 1:4.

Figure 5:
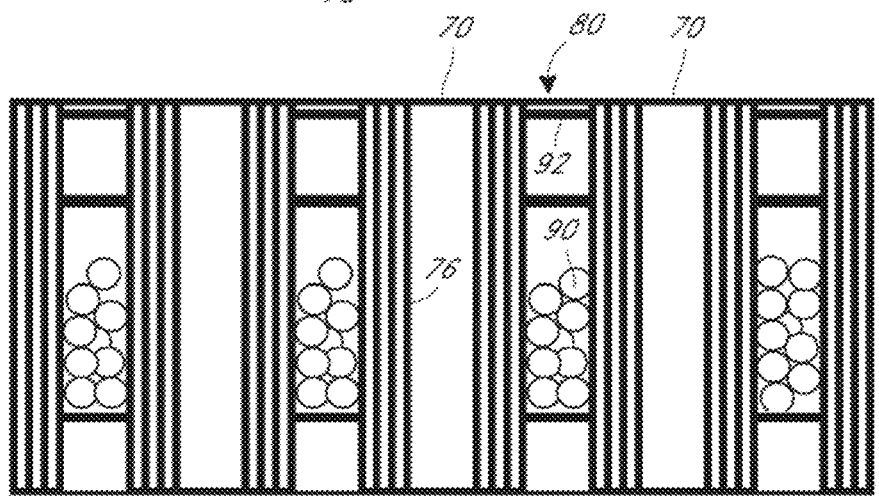
FIG. 5 is a side view of a portion of a beam selector with an adjustable focal point using x-ray-absorbent beads that block scatter from selected locations of the rear detector.

Alternatively, as shown in FIG. 5, the region 80 between the tubes 76 is blocked at both sides by plates 92 of polymers, elastomer, smart metals, and/or some combination of these. The region 80 is filled with beads 90 or powders of x-ray-absorbent materials. The thickness of beads 90 or powders is adjusted as necessary to attenuate x-rays as desired.

Alternatively, smart metals and/or smart wires connect the tubes 64. The smart metals and/or wires can stretch, compress, or bend in at least one dimension under computer control.

Figure 6:
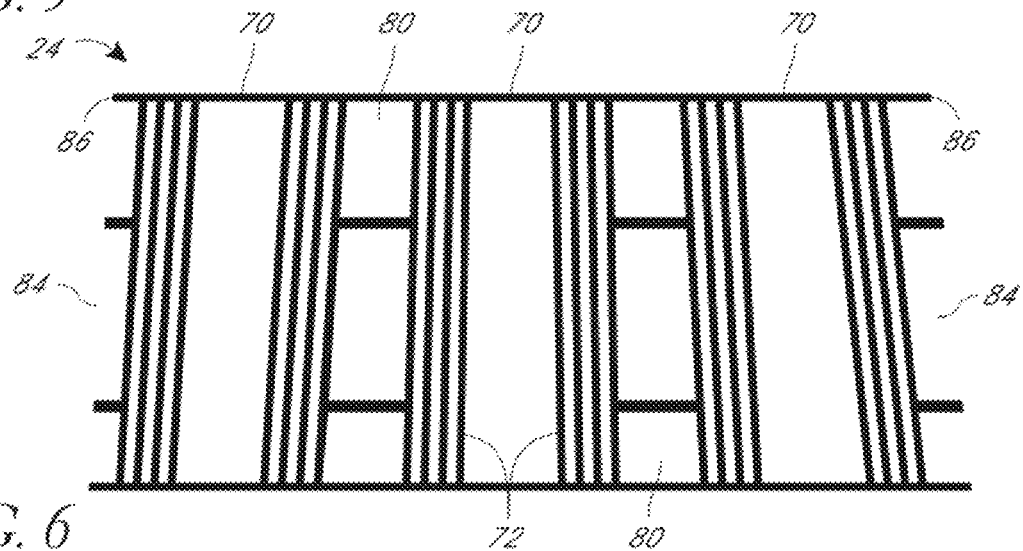
FIG. 6 is a side view of the portion of the beam selector of FIG. 4 adjusted to a focal point.

Typically, in its quiescent state, the holes 70 are parallel to each other and have no focal point. In order to create a focal point, the top edges 86 of the four sides 84 are displaced inwardly, as in FIG. 6. Assuming that the four sides 84 are of equal length and that the compressibility of the region 80 is constant throughout the beam selector 24, displacing all four edges 86 by the same amount will produce a focal point above the center of the beam selector 24. The distance of the focal point will depend on the amount of displacement. By varying the amount of displacement of each edge 86 individually, the location of the focal point can be changed in three dimensions. To achieve a focal point (as opposed to a focal line), at least two adjacent edges 86 must be displaced.

Alternatively, the region 80 between the tubes 76 is not x-ray-absorbent. As long as the tube walls 78 comprised of one or more x-ray-absorbent materials block substantially all of the scatter 34 from the selected locations 38, the region 80 only needs to be filled with a polymer, elastomer, and/or any materials which can provide enough structural support.

Another example of a beam selector is a focused or parallel grid, line grid, or crisscross grid formed by two line grids. A line grid is generally comprised of alternating lines of x-ray-absorbing material and space, or materials of non-x-ray-absorbing properties and low-x-ray-absorbing properties. The x-ray-absorbing material lines block the primary x-rays and the alternate spaces allow the transmission of primary x-rays. A crisscross pattern or line grid version may be variations of the 2D beam selector mentioned above, where the layout where the primary x-ray has come through is determined by the area where low-x-ray-absorbing materials or non-x-ray-absorbing materials are placed. A focused grid is where the regions of the grid where the primary x-rays pass through is designed so that the geometry of x-ray fan beam is taken into consideration. The focal point of the primary x-ray regions is aligned with the x-ray fan beam passage way, so that primary x-rays are transmitted at distributed regions on the detector. The configurations described here are slight variations of previously described beam selectors using commonly used grids in x-ray collimators.

Another embodiment of a beam selector 24 with an adjustable focal point is shown in FIGS. 7-13. The beam selector 24 allows only primary x-rays 32 through to selected locations 38 of the rear detector 26.

Figure 7:
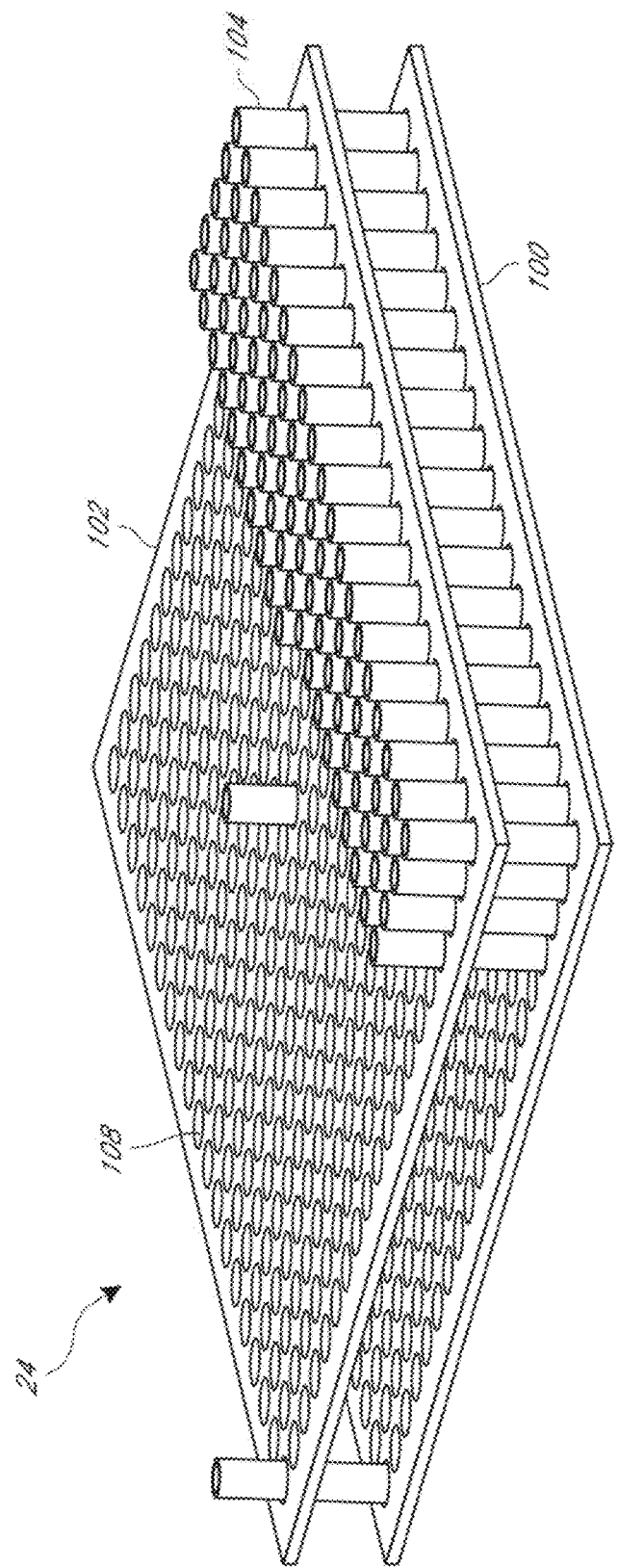
FIG. 7 is a perspective view of a beam selector with a movable focal point using rigid materials and showing some of the tubes.

As shown in FIG. 7, in one configuration, the beam selector 24 comprises two or more rigid, x-ray-absorbent plates 100, 102 with a large number of rigid, hollow tubes 104. The tubes 104 are formed of x-ray-absorbent materials or polycapillary tubes capable of total internal reflection of beams at the restricted critical angle or non-x-ray absorbent materials that do not generate scatter so long that such setup does not allow scatter to pass through the tubes 104 and upper plate 102 and impinge on the detector at the bottom of other tubes. The tubes 104 can be formed like those of the beam selector embodiment of FIG. 4.

The beam selector embodiments above that allow only primary x-rays 32 through to selected locations 38 of the rear detector 26 employ hollow tubes 104 with x-ray-absorbent walls. The present disclosure contemplates that alternatives to the tubes 104 can be used.

Optionally, for the embodiments shown in FIG. 7, beads or powders of x-ray-absorbent materials are added in a pocket made of metal or polymer surrounding each tube 104 immediately above the rear detector 26. The thickness and width of the pocket are designed to block substantially all (99.99%) primary x-rays 32 and scatter 34 from reaching the rear detector 26 around the tube 104, thereby creating an area devoid of any x-ray signals surrounding the selected locations 38.

Optionally, for the embodiments employing elastomers, beads and/or powders of x-ray-absorbent materials can be used between the plates 100, 102 without elastomers.

Figure 8:
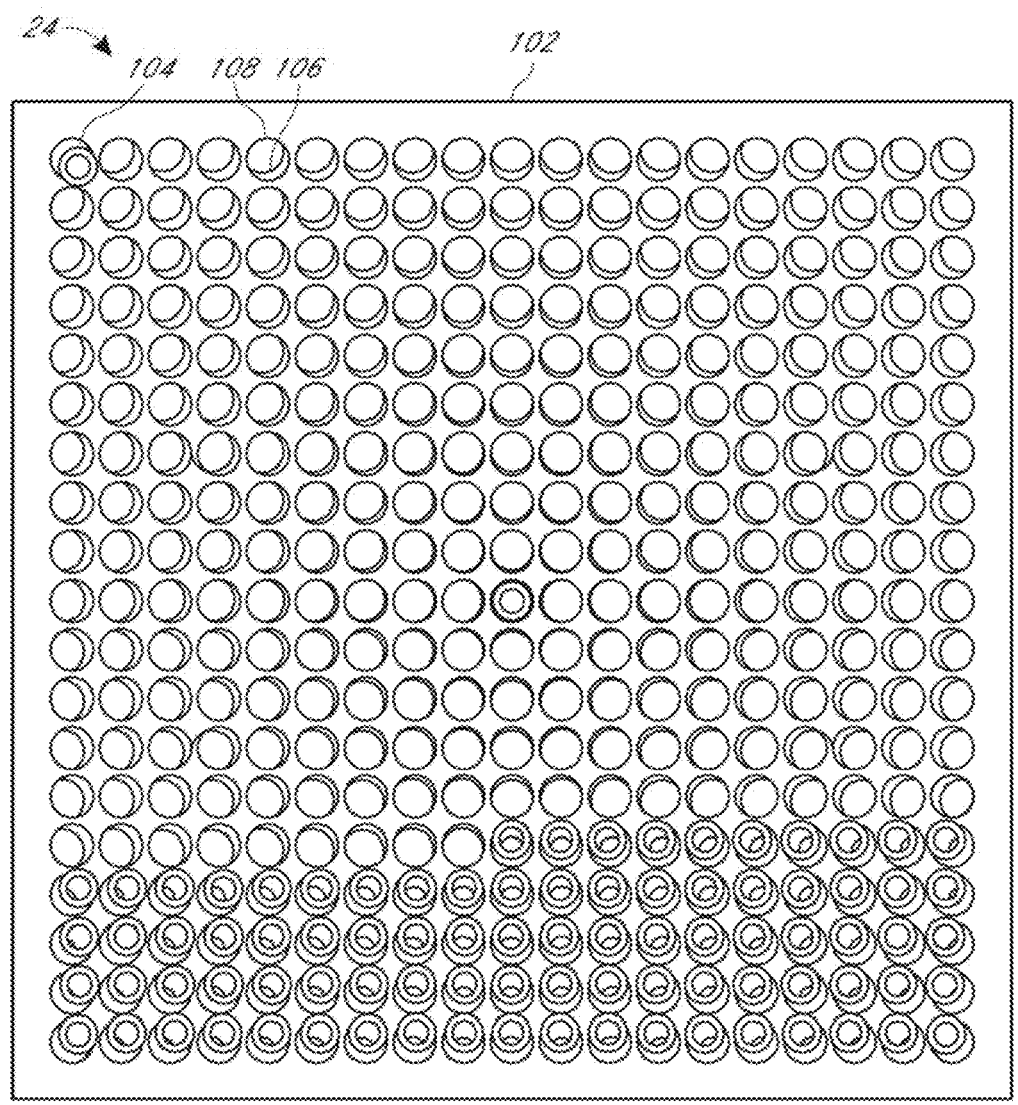
FIG. 8 is a top view of the beam selector of FIG. 7.

In one configuration of an adjustable focal point beam selector, the base plate 100 has a square matrix of apertures 106 of a given pitch and the focusing plate 102 has a square matrix of apertures 108 with a pitch that is slightly smaller than that of the base plate 100, as seen in FIG. 8. For example, if the base plate pitch is 10 mm, the focusing plate pitch can be 9.8 mm.

The base plate apertures 106 are slightly larger than the diameter of the tubes 104 so that the tubes 104 can tilt within the aperture 106 to an angle of about 11° from vertical for a focal length of 500 mm. The focusing plate apertures 108 are slightly larger than the diameter of the tubes 104 so that the tubes can slide within the apertures 108 and tilt within the aperture 108 to an angle of up to about 11° from vertical for a focal length of 500 mm.

Figure 9:
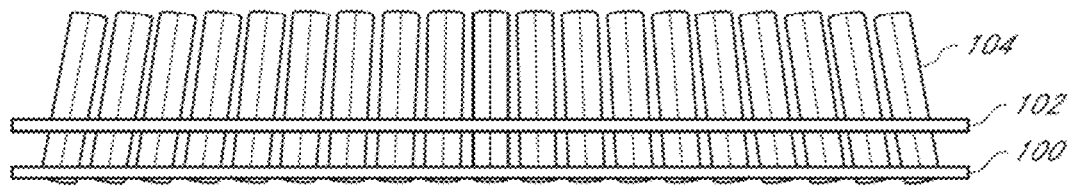
FIG. 9 is a side view of a beam selector of FIG. 7 adjusted to a nearer, center focal point.
Figure 10:
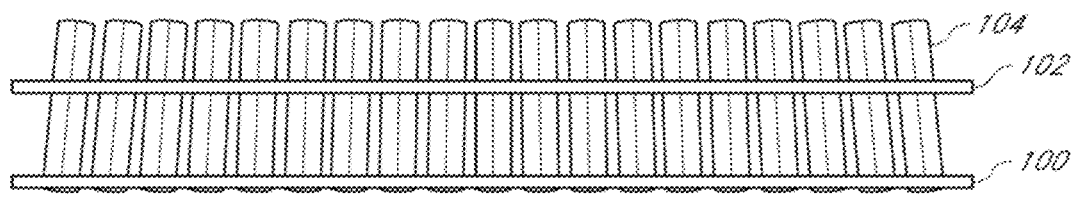
FIG. 10 is a side view of a beam selector of FIG. 7 adjusted to a middle-distance, center focal point.
Figure 11:
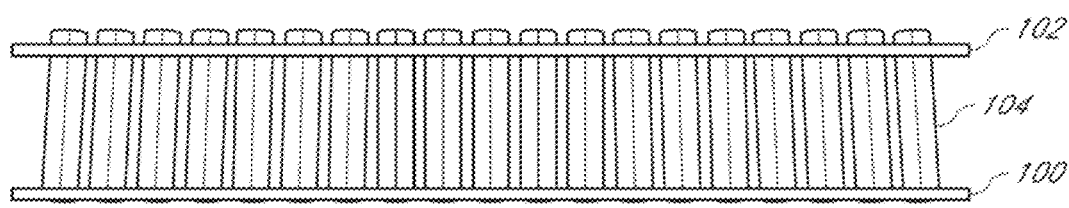
FIG. 11 is a side view of a beam selector of FIG. 7 adjusted to a farther, center focal point.
Figure 12:
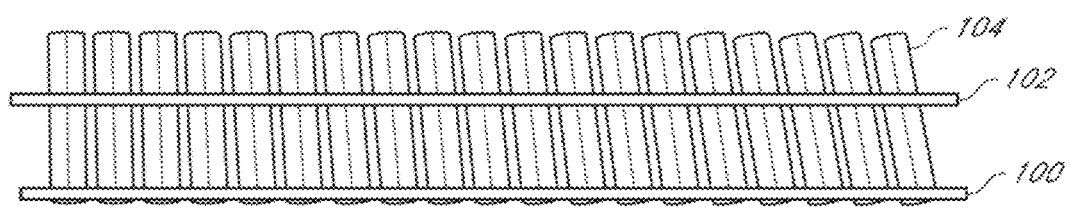
FIG. 12 is a side view of a beam selector of FIG. 7 adjusted to a middle-distance, left edge focal point.
Figure 13:
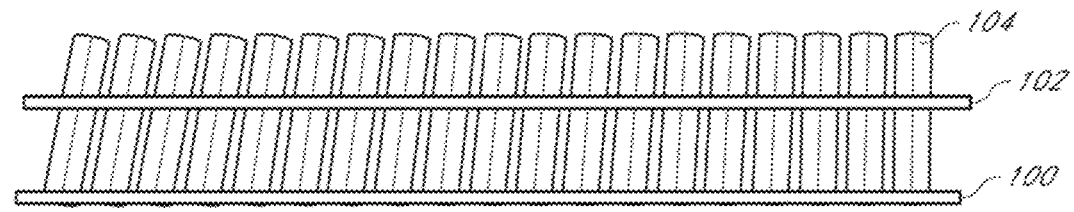
FIG. 13 is a side view of a beam selector of FIG. 7 adjusted to a middle-distance, right edge focal point.

When the focusing plate 102 is centered on the base plate 100 such that the center tube 104 is vertical, the focal point is directly above the center of the focusing plate 102. As shown in FIGS. 9-11, moving the focusing plate 102 vertically changes the vertical position of the focal point. As shown in FIGS. 13 and 13, moving the focusing plate 102 horizontally changes the horizontal position of the focal point.

In one configuration, the beam selector 24 has an array of total internal reflection elements, such as polycapillary conduits, where only x-ray beams that strike the conduits at a very narrow range of critical angles are passed through to the rear detector 26.

Figure 14:
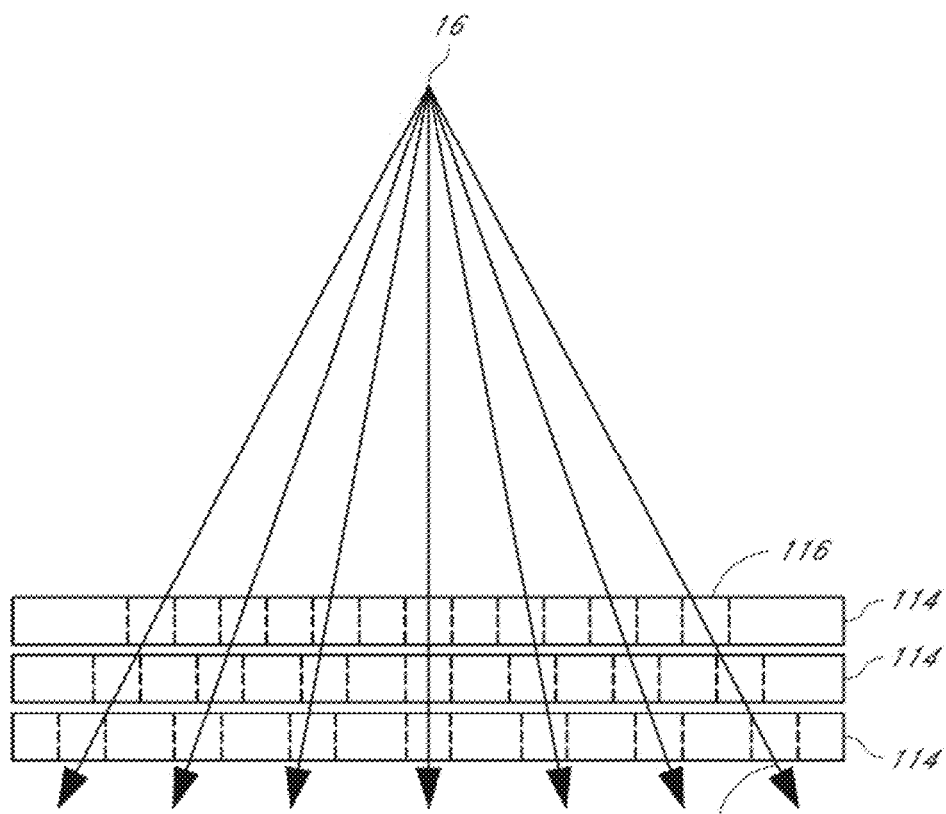
FIG. 14 is a side view of a beam selector with a movable focal point using stacked plates.
Figure 15:
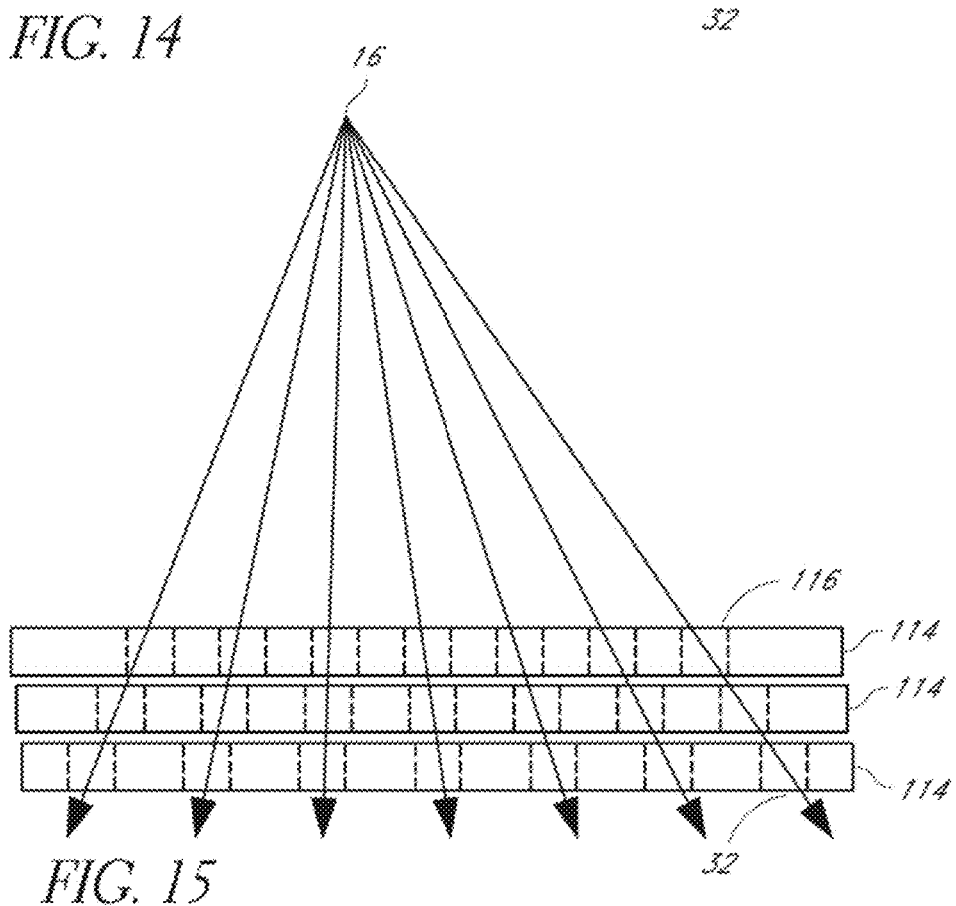
FIG. 15 is a side view of the beam selector of FIG. 14 adjusted to a different focal point.

Another example of a beam selector 24 with an adjustable focal point is shown in FIGS. 14 and 15. In this embodiment, the tubes are eliminated and perforations 116 are located in multiple stacked plates 114 of x-ray-absorbent materials with thicknesses designed to absorb substantially all of x-rays. The perforations 116 align to form the holes 118 that pass primary x-rays 32 to the rear detector 26. The plates 114 are moved along each other by 2D actuators in order to shift the focal point.

In another configuration, the beam selector 24 comprises x-ray optics, for example, an array of diffractive elements such as static and spatially-tunable or modulated MEMS or deformable MEMS, and crystals, such as ultrasound modulated spatially-tunable crystals for x-ray transmission at selected regions, or diffractive gratings and related x-ray optics.

When the direction of the incoming x-ray beam illuminating the crystal is varied, the modulation may change or remain the same correspondingly to allow primary x-rays to pass through.

The beam selector 24 can have an array of refractive elements, such as x-ray optics or x-ray lens assemblies.

Separating primary x-rays or scatter can be based on the critical angles for incident x-ray beams. One bean may be within the critical angle and the other beam may be outside of the critical angle combined with the use of x-ray optics. For example, using refractive x-ray lenses as part of the beam selector, separation of primary x-ray or scatter may be based on the acceptance angles for incident x-ray beams. In some instances, such a beam selector could be part of a front window of the rear detector which allows x-rays of selected regions to pass through and be detected, thereby separating primary x-rays and scatter. Alternatively, the direction of the signals received at the rear detector corresponds to the incident angle of the x-ray beams, and with a known x-ray emitting location, geometry, and predicated incoming x-ray beam angle, the primary x-rays and scatter are differentiated at the rear detector.

The configurations described above that employ scatter blocking beam selectors can also use a full 2D rear detector 26. In these configurations, the detector cells 28 that are not aligned with the holes 48 are not used because they are blocked from receiving any x-rays by the beam selector 24.

Figure 18:
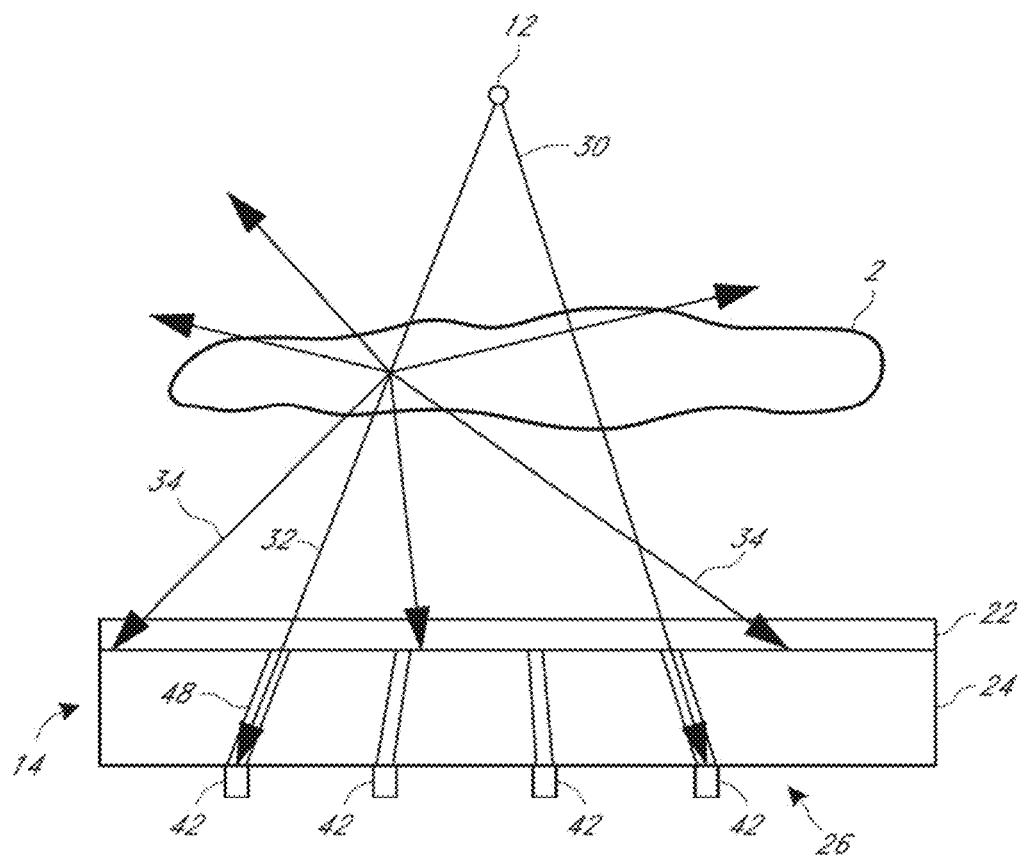
FIG. 18 is a side view of a detector assembly having a scatter-blocking beam selector and rear detector cells only at the base of the holes.

Alternatively, as shown in FIG. 18, rather than employing a full 2D detector, the rear detector 28 comprises groups 42 of one or more detector cells 28 where each group 42 is positioned at the base of a beam selector hole 48.

A variation of the configuration comprising the beam selector sandwiched between two detectors is to use a dual-detector layer. In one example, the front detector is selectively transmissive of either primary x-rays or scatter while being able to detect the projected image that includes both primary x-rays and scatter. Areas of pixels which are transmissive regions comprise at least one transmissive pixel. In one example, the front detector has a checker board pattern, with alternating transmissive where primary x ray can pass through and opaque regions. The alternating pattern and dimensions of the two regions are determined by the requirement of the application and what percentage scatter needs to be removed or separated from the primary x-rays. In one example, below a transmissive area which comprises one or more pixels, a single diode or multiple diodes with one pixel in each diode may be used as detectors. Alternatively, a small detector with one or multiple pixels may be used. Thus, in place of a planar rear detector, there need not be a single detector, but rather multiple small detectors, each smaller than the front detector.

In another configuration, each pixel of the front detector is partly transmissive and partly senor. The rear detector captures the transmitted signal coming out of the front detector.

In another variation, such transmissive or transparent features may be built into the rear detector. Therefore x-rays may be absorbed or transmitted in the rear detector before the sensing region of the rear detector.

Alternatively, such a detector assembly is built into one detector with features built-in as described above and dual detecting planes.

Another variation of a beam selector uses filters for reducing the proportion of scatter reaching the second detector layer and a first sensor attached to the filter to capture both primary x-rays and scatter.

Yet another example of a beam selector 116 placed between the front detector and rear detector comprises two or more plates, 114, as illustrated in FIG. 14 and FIG. 15. Each of the plates comprises an x-ray absorbing material, such as tungsten, copper, or an alloy. The thickness of each plate may be such that either alone or combined, it can absorb almost all of the x-rays at one or more energy levels. There may be a spacer between the plates to maintain a distance between plates. Optionally, an x-ray-absorbing frame around the four sides of the plates not facing the detectors is placed as a beam stopper.

Each of the plates may have holes of various shapes. If the first plate 114 is the plate closest to the front detector, the second 114, third 114, fourth 114, fifth plate 114, may have corresponding holes of similar or larger size to those of the first plate 114.

In some instances, each plate 114 may be moved by one or more linear actuators to align the x-ray source and holes distributed across each plate to allow the primary x-rays to pass through.

Alternatively, if the holes are larger on the plates closer to the rear detector, there may be no need to move the plates. Only areas on the detector where the primary x-ray beam paths are projected are used as the selected primary signals. Any x-ray signal outside of the beam path will not be considered in derivation of a high-resolution primary x-ray signal on the front detector. These areas where the primary x-ray beam path project may be predetermined by the relative location of the x-ray source to the detector and the position of the beam selector plates, or by measurements done without the imaged subject, but with varied x-ray emitting positions corresponding to imaging configurations with the imaged subject.

X-Ray Source and Emitting Locations

The present disclosure uses an x-ray source 12 that is capable of emitting pulsed or continuous x-rays with controllable energies. Such an x-ray source can be conventional x-ray tube x ray sources, cold-cathode x-ray sources, metal-liquid jets, laser Compton x-rays, linear accelerator based x ray source, or synchrotron or synchrotron-like x-ray sources, coherent or partially coherent x-ray sources, monochromatic sources, broad spectrum x-ray sources and/or field emitter nanostructure based x ray sources.

Examples of an x ray source include a plurality of individually programmable electron emitting units for emitting an electron beam when an electric field is applied, an anode target that emits an x-ray beam when subjected to collision of the electron beams emitted from an x-ray source having a collimator.

Each electron emission unit can comprise an electron field emission material. Each electron field emission material can comprise a nanostructured material. The electron field emission material can comprise a plurality of nanotubes or nanowires. Examples of the nanotubes (including carbon, boron and/or nitrogen) comprise at least one field emission material selected from the group consisting of sulfur and/or tungsten. Examples of the nanowires (including silicon, germanium, carbon, oxygen, indium, cadmium, gallium, Zinc, oxides and/or nitrides) can comprise at least one field emission material selected from the group consisting of silicides and/or borides.

Examples of a Portable Field Emitter Nanotube Based x Ray Source

X-Ray Source for Portability

Figure 32:
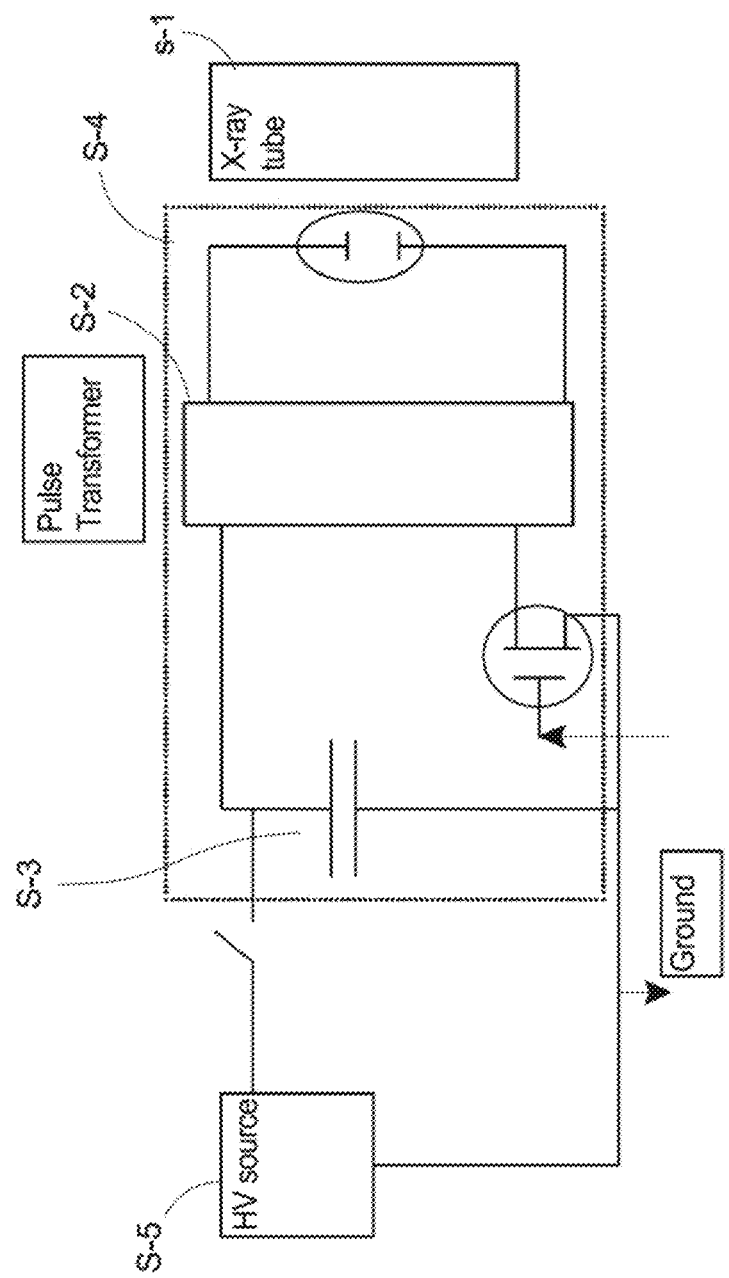
FIG. 32 is an example of an x-ray source.

The present disclosure provides an x ray source, an example of which is illustrated in FIG. 32. It includes An x ray generator with high efficiency, low weight and compact size. For example, a vacuum-sealed field emission tube, s-1. S-1 can comprise a cold cathode x ray tube;

Electric energy storage, for example, a condenser or capacitor, for storing the electric energy of the pulse operation, s-3. S-3 can be built at a pre-stage, can work at a much lower voltage, for example, between 5 kV and 10 kV.

A voltage Amplifier, S-2 for example, a high voltage pulse transformer, to provide high energy pulse, for example, from 100 kV-150 kV.

The pulse duration may be controlled, for example, between 0.1 ms and 10 ms. The corresponding current flowing in the tube may be between, 10 m A and 1 A to provide the desired amount of energy for a quality x-ray imaging. The pulse width and the current is determined by the parameters of the capacitance of the condenser, the inductance of the pulse transformer, and the V-1 characteristic curves of the tube.

Figure 31:
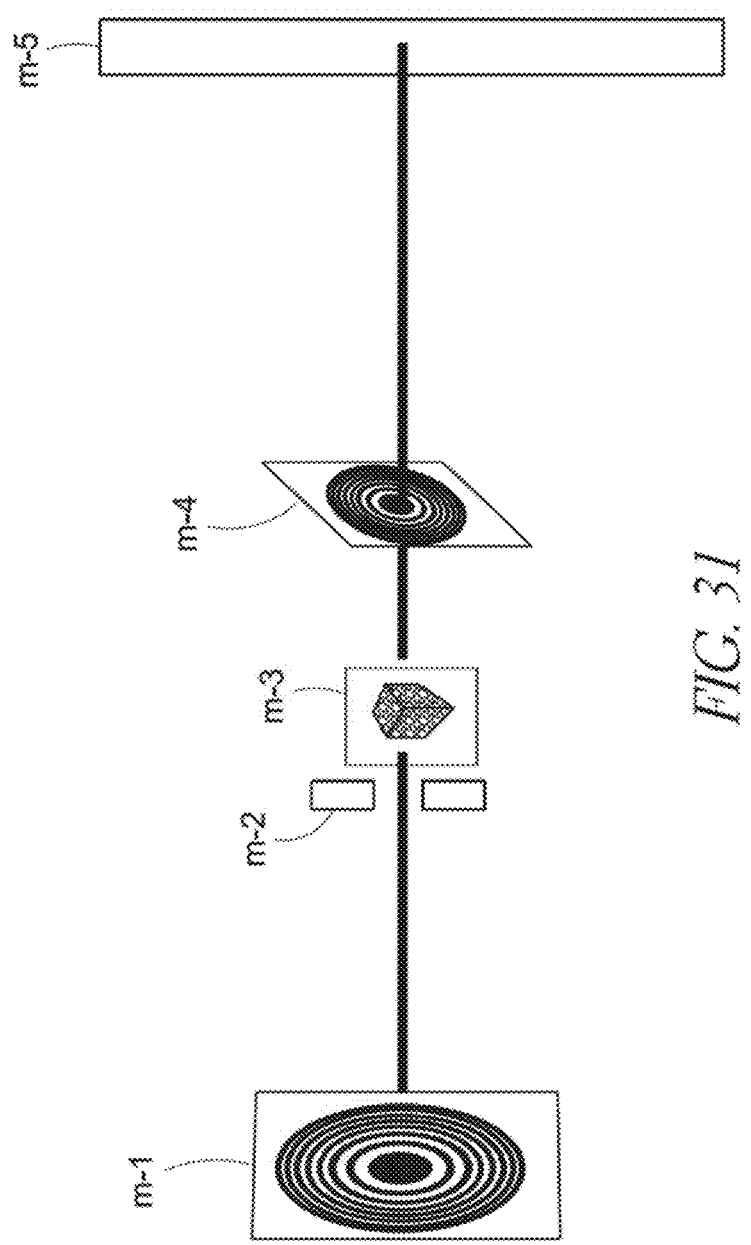
FIG. 31 illustrates a configuration of x ray microscopy.

Flash x-ray sources can be based on use of a field emission tube driven by for example, a high voltage source which provides high current output, to trigger the pulse transformer. For example, HV semiconductor devices, HV tryrister-triggered pulse transformer or integrated gate bipolar transistor, such as illustrated in FIG. 31. Vacuum or Gaseous type of devices, such as Thyratron Spark Gaps, are examples of High Voltage (HV) devices, which can provide HV pulser with high current output.

High Voltage Thyrister or IGBT can serve as the switching device, S-5. Two or more such HV devices may connect in series to reach the initial HV voltage required to provide high current output such as a voltage in between 5-15 KV.

For variable energy generation at the output of the x ray source, different targets on a rotating anode, each generates x ray of a certain energy level, is used.

Figure 23:
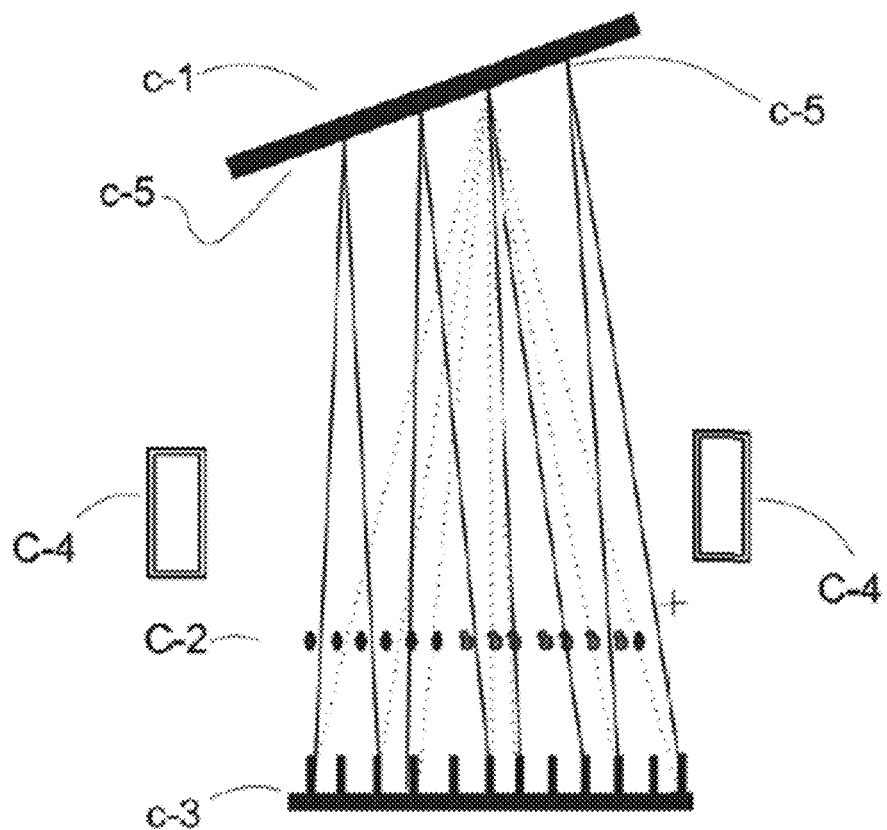
FIG. 23 illustrates a NanoTube field emitter system.

X ray tubes maybe based on cold cathode x ray tubes. For example, field emission x ray source, comprising a plurality of programmable electron emitting unit, where each electron emitting unit maybe focused by either a cone shipped anode target or a focusing means such as a electrostatic lens, electrooptic focusing lens as described above. The gate mesh illustrated in FIG. 23-24C is optional.

The present disclosure provides an x ray source comprising major components with typical parameters: including for example, a 2.5 kV DC power supply, a high voltage current storage means such as a condenser with a capacitance, for example, 2 μF, an electronic triggering circuit, a high voltage pulse transformer, in one instance, encapsulated in Sylgard Silicone, and an x-ray tube, which may be a cold cathode x ray source. The total energy stored in the condenser for generating a single x-ray pulse maybe 30 J when HV=50 kV. The dimension of the whole x-ray source maybe less or about 8"×8"×16", with a weight of about <30 lb. A smaller dimension is possible depending on the choice of each component. The X ray energy level can be between 125 KV to 250 KV.

Such an x ray source maybe used in a two dimensional imaging system, and may have portable capabilities.

Figure 20:
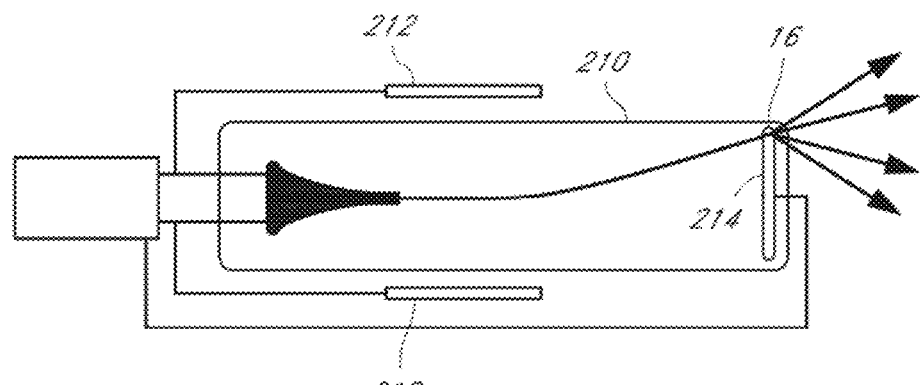
FIG. 20 is a schematic view of an x-ray source using magnetic deflection.

To provide a tomography system with no moving parts, as illustrated by FIG. 20, the electron beams or charged particle beams maybe steered by magnetic means such as magnetic plates or magnetic based steering device or metal means, electrooptic lens for example, in a system with multiple dimensional imaging capabilities as described in the present disclosure.

The x ray source device may generate single or multiple energies. It can be used for one or more of the systems described below, A x ray system of single, dual or multiple energy
A x ray system with scatter and primary x ray separated involving hardware and software
A x ray multiple dimension or 3D imaging system
x ray imaging system for diagnostics, industrial and research applications.
Typical Parameters of the source
Focus: 0.1 mm to 10 mm
Screen area: 60 cm×60 cm
Typical scan point: 30×30 to 50×50, maximum
Dwelling Time at one spot: 0.01 ms to 10 ms
Typical Time at one spot: 1 ms
For one complete set of image, determined by the detector frame rate.

The source 12 can emit two or more consecutive x-ray pulses with controllable energies for each imaging operation: a high-energy pulse at an average energy level H followed by a low-energy pulse at an average energy level L. Each pulse has a single, reproducible energy spectrum, which comprises bremsstrahlung radiation and discrete line emissions.

In another configuration, the source 12 emits three consecutive pulses for each imaging operation: a high-energy pulse at an average energy level H, followed by a medium-energy pulse at an average energy level M, followed by a low-energy pulse at an average energy level L. Each pulse has a single, essentially unchanged energy spectrum.

In another configuration, the source 12 emits a pulse which has two or more energy peaks each separated from the other energy peaks temporally within the pulse duration.

In another configuration, the source 12 emits a broad spectrum pulse.

Each of the detectors or x ray measurement assembly including the detectors may be energy sensitive, such as photo diode arrays or energy sensitive detectors or x ray spectrometer.

Movement of the x-Ray Emitting Locations

The x-ray emitting position may be moved by mechanical, electrical and/or magnetic energy means.

Figure 19:
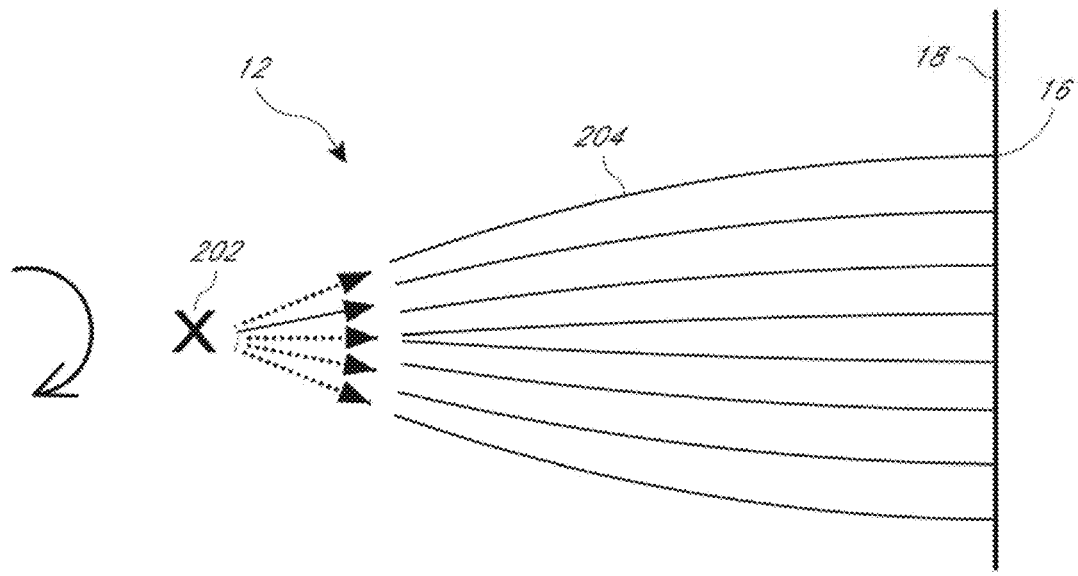
FIG. 19 is a schematic view of the x-ray source using the total internal reflection of polycapillary tubes to produce x-ray beams emitted from different locations.

With reference to FIGS. 1 and 19, the x-ray emitting location 16 can move relative to the subject 2 in a plane 18 parallel to the detector assembly 14. Alternatively, the present disclosure contemplates that the emitting location 16 can move relative to the subject 2 in a plane perpendicular to the detector assembly 14 or in a plane other than parallel and perpendicular to the detector assembly 14. A mechanical, electrical or magnetic mechanism provides the desired motion.

In another configuration, the mechanism moves the emitting location 16 either angularly, linearly, or a combination of both. The movement is preferably done to solve the unknown pixels in the third dimension in the region of interest 4 within the subject 2, preferably in integer multiples of pixel pitch, while minimizing the introduction of new unknown pixels in each movement and minimizing introduction of a total number of new unknown pixels for the complete derivation of unknown pixels in the third dimension for the region of interest 4.

To minimize total imaging time and radiation exposure, the present disclosure contemplates, though does not require, that the mechanism provides the emitting location 16 motion rapidly. For example, the mechanism can provide this motion in increments of integer multiples of pixel pitch (the distance between adjacent detector cells 28).

The present disclosure contemplates that the subject 2 is physically moved relative to the emitting location 16, particularly in applications, such as industrial applications, where the subject 2 is already in motion while being imaged. To minimize total imaging time and radiation exposure, each movement, either angular or linear, resolves the unknown pixels in the third dimension, preferably in integer multiples of pixel pitch and at the same time, new unknown pixels are introduced in the process, the number of measurements required to resolve such unknown pixels in addition to the region of interest will need to be taken into account.

One example of an x-ray source and movement system is a metal, graphene, silicon or carbon nano-tube-based field emitter, which is driven by an applied electric field, not by temperature, that is also known as a "cold cathode". In a CNT, the current is exactly and instantaneously controlled by an applied voltage.

A CNT emitter, c-3, can be used in the x-ray tube including two or more field emitter nanotubes such as carbon nanotubes, arranged vertically on a conductive substrate. In one configuration, the width of carbon nanotubes is in the nanometer range. The tip of the carbon nanotube is where the emission occurs. In one example, the CNTs are arranged as illustrated in FIG. 23. A grid or a gate mesh structure, c-2, connected to an electrode inside the tube wall is placed a small distance above the tips of the CNT. A voltage gradient may be applied externally between the grid mesh and the substrate. The voltage generates a very strong electric field at the tips of the CNTs. The electric field strength concentrated at the CNT tips forces field emission of negatively charged electrons to occur at the tips of the CNTs. When the exposure is switched on, the electrons are emitted from the CNT tips and fly toward the grid mesh, c-2. The majority pass through to be accelerated by the anode high voltage, generating x-rays when the electrons impact the anode c-1. The electro-optic focus lens, c-4, which can be inside, can be used to dynamically adjust the focal spot size of the x-ray emission or to move the focal spot on the anode to different locations.

Figure 24A:
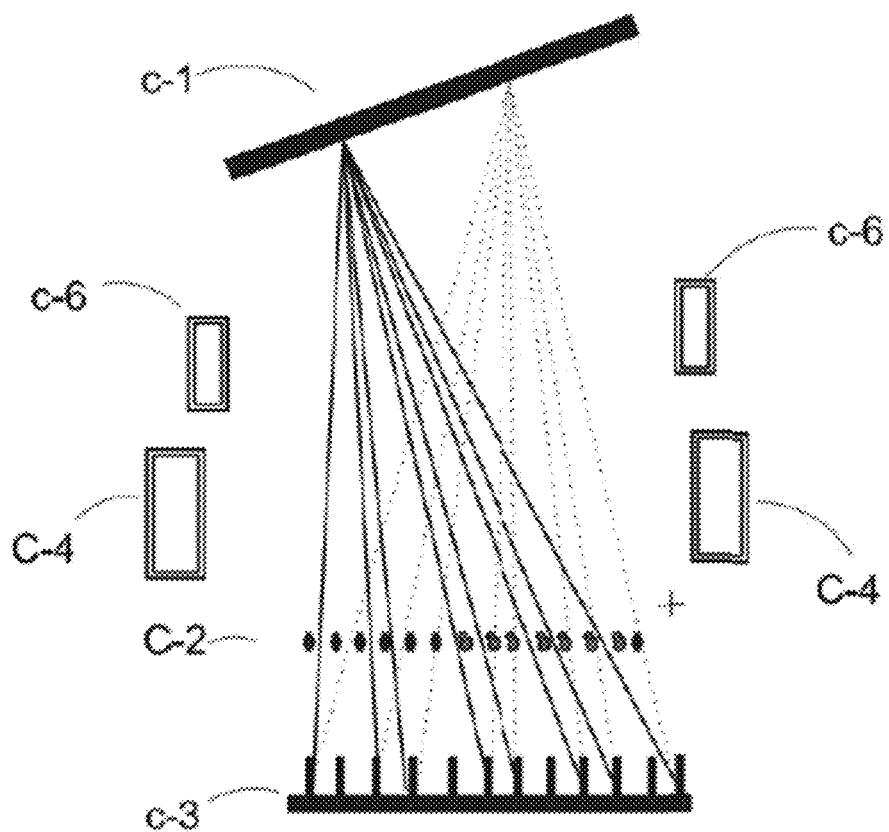
FIGS. 24A-C illustrate configurations of field emitter activation zones.

As illustrated in FIG. 24A, different regions of CNT emitters may be activated, combined with using the electro-optic electrodes c-4 to control the electron beams to adjust the size of the focal point of the electrons c-5 on the anode.

To control the size of electrons on the focal point, other types of electrostatic lens or electromagnetic lens can be used, for example, an electromagnetic coil, einzel lens, quadrapole lens, magnetic lens, or multipole lenses.

An additional electromagnetic means for example, an electromagnetic coil c-6 may be used to steer the beam so that the x-ray beams may be emitted from various locations on the anode from the XY plane parallel to the detector. In another embodiment, for electronic beam steering, a set of magnetic plates, or metal plates may be used.

Figure 24B:
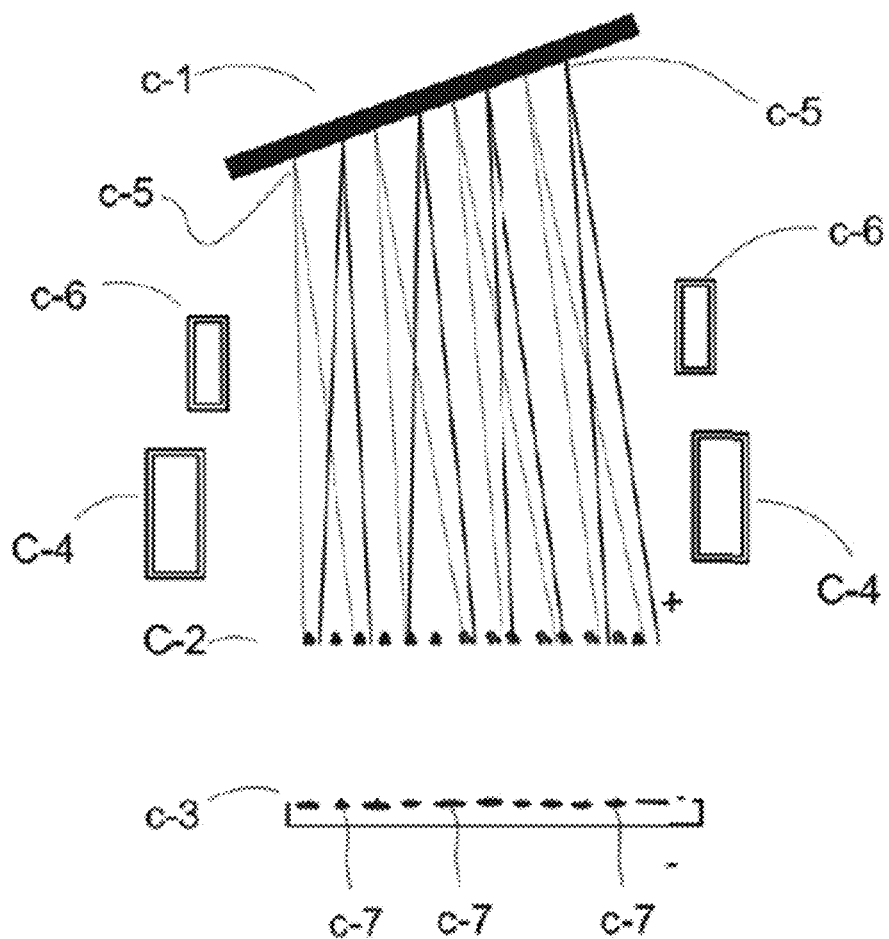
Figure 24C:
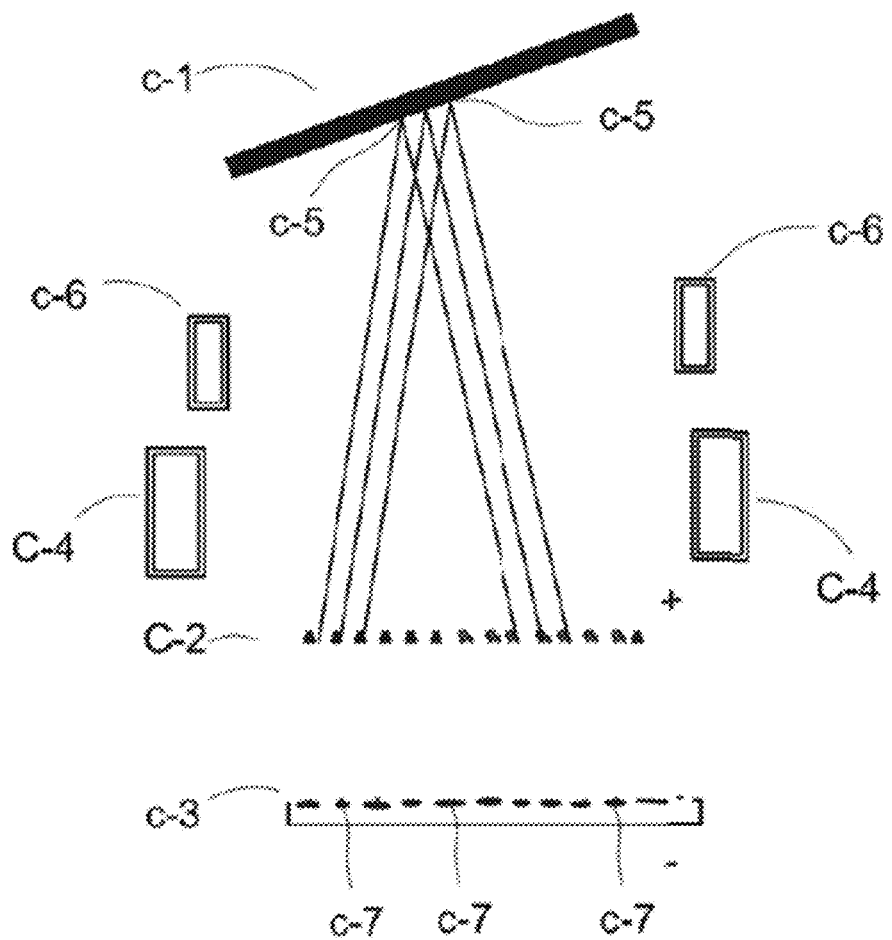
Figure 25:
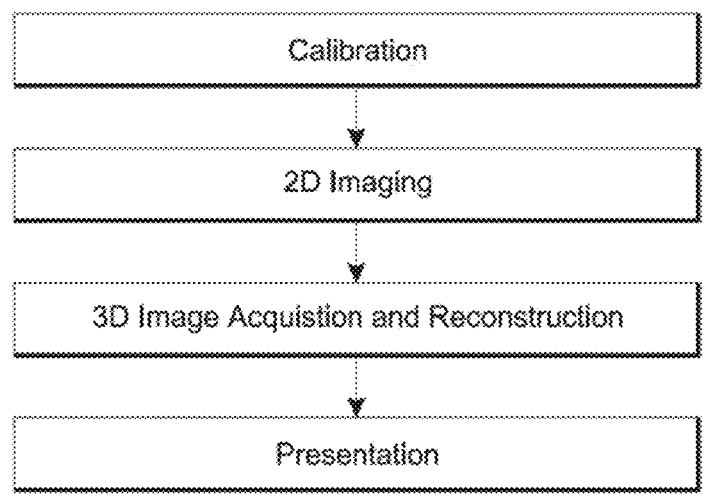
FIG. 25 is a flow diagram of the basic steps of the 3D imaging methods.
Figure 26:
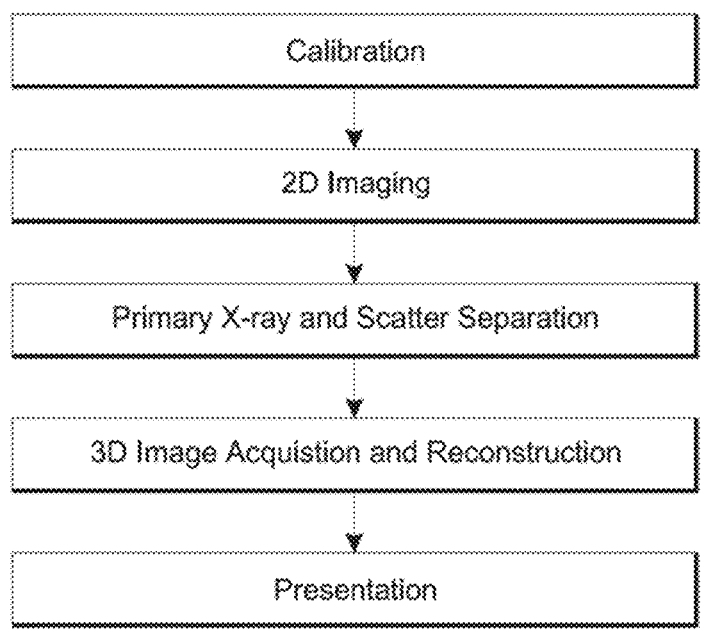
FIG. 26 is a flow diagram of the basic steps of the 3D imaging methods with a step added to separate primary x-rays and scatter.
Figure 27:
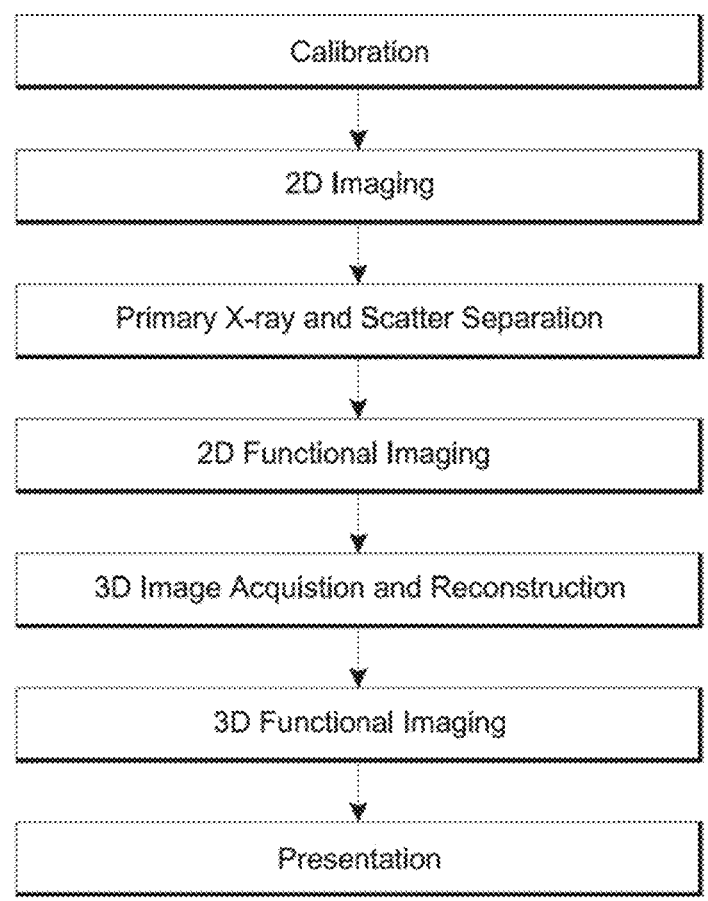
FIG. 27 is a flow diagram of the basic steps of the 3D imaging methods with steps added for 2D and 3D functional imaging.
Figure 28:
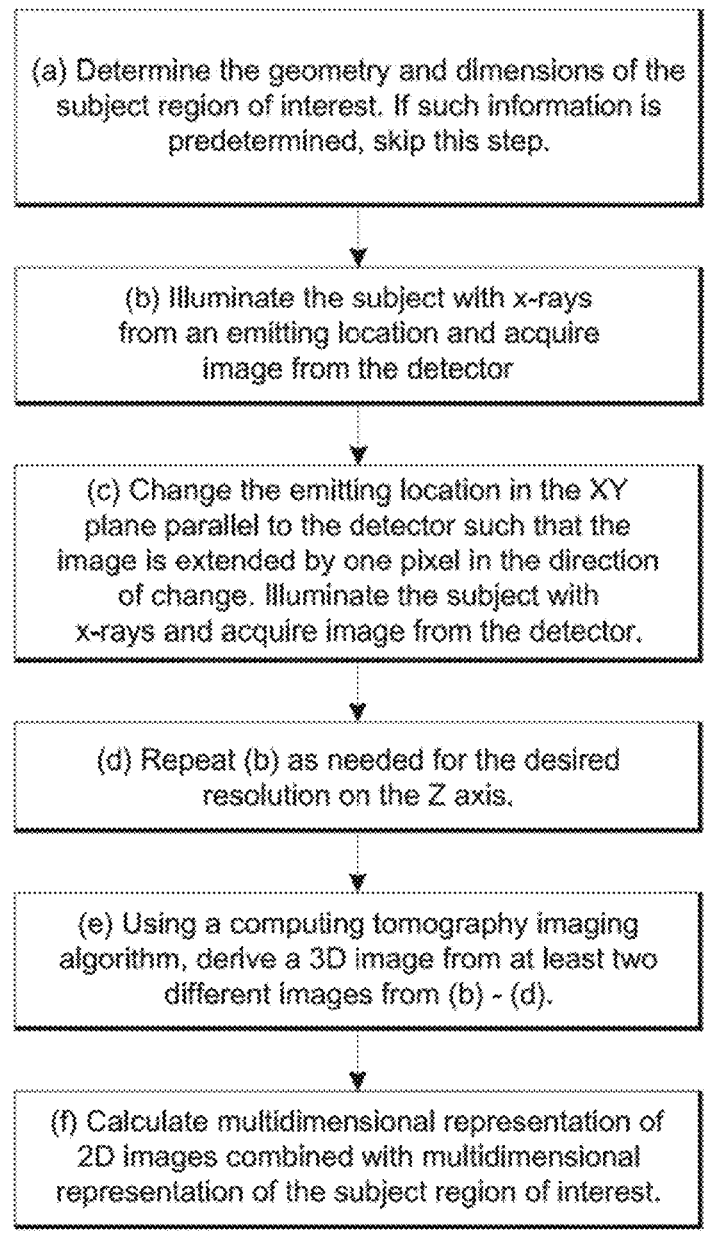
FIG. 28 is a flow diagram showing multidimensional imaging from at least two 2D images taken at two different x-ray emitting positions.
Figure 29:
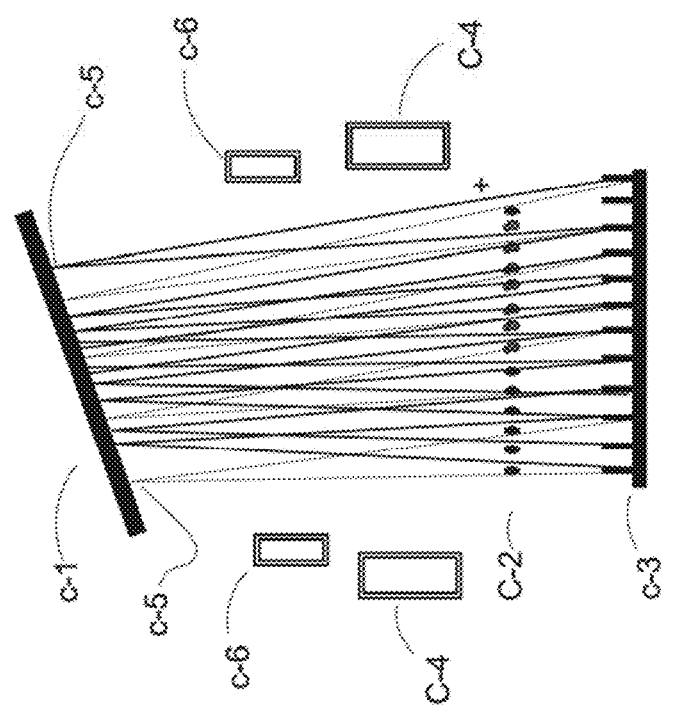
FIG. 29 is a schematic of a steering electron beams in a x ray tube with programmable field emission units.

In one configuration, CNT emitter element c-3 comprising regions c-7, each comprising one or more field emitter nanotube emitters as illustrated in FIGS. 24A, 24B and 24C, different implementations of this configurations. Each region may be activated and deactivated independently from the others. Electron beams originating from one or more field emitter nanotube emitters may be steered electronically by electrooptical devices or magnetically by magnetic plates or electromagnetically by electromagnetic coils c-5 so that its focal spot on the anode may shift its position in a programmable pattern. The overall x-ray emitting positions on the anode may be extended in area or distance by using two or more such regions, for instance, so that the pattern of x-ray emitting positions may be continuous throughout the x-ray emitting area on the anode.

With specific reference to systems that use a beam selector, such as beam selector 24. Some beam selector embodiments must remain fixed relative to the emitting location 16 because they have fixed focal points, and other beam selector embodiments do not have to remain fixed relative to the emitting location 16 because they have adjustable focal points.

Several different mechanisms for providing a moving emitting location 16 and, optionally, a moving detector assembly 14 are described below.

In one mechanism, two or more x-ray sources 14 are positioned at different locations in the plane 18 and emit pulses sequentially from those locations. The detector assembly 14 is fixed. For this mechanism, the beam selector 24 must have either multiple fixed focal points or an adjustable focal point.

In other mechanisms, a single x-ray source 12 emits x-ray pulses sequentially from different locations on the plane 18. The present disclosure contemplates several different configurations that can accomplish this.

In one configuration, a two-dimensional actuator physically moves the x-ray source 12 and the x-ray detector assembly 14. Preferably, the actuator can move the x-ray source 12 and the x-ray detector assembly 14 an integer multiple of one detector pixel pitch in the plane 18 at or faster than the frame rate of the detector assembly 14. For this configuration, the beam selector 24 can have a fixed focal point.

In another configuration, a two-dimensional actuator physically moves only the x-ray source 12. Preferably, the actuator can move the x-ray source 12 in the plane parallel to the detector assembly 14 in increments of the minimum integer multiple of pixel pitch, which leads to a planar motion of one-pixel pitch for an x-ray beam measurement location relative to the previous position, at or faster than the frame rate of the detector assembly 14. For this configuration, the beam selector 24 must align with the emitting location 16. In some configurations, the beam selector 24 may need to have an adjustable focal point.

In another configuration, a two-dimensional actuator physically rotates only the x-ray source 12 so that the emitting location 16 moves in an arc. Preferably, the actuator can rotate the x-ray source 12 the equivalent of an angle along the arc to simulate a planar motion of one pixel pitch, or an integer multiple of one detector pixel pitch at or faster than the frame rate of the detector assembly 14. For this configuration, the beam selector 24 must align with the emitting location 16 and, in some configurations, may need to adjust its focal point.

In another configuration, shown in FIG. 19, the x-ray source 12 is a single x-ray source 202 and the x-ray beam is moved to different emitting locations 16 using total internal reflection of, for example, polycapillary tubes 204.

In other mechanisms, methods are used to deflect the electron beam within the x-ray source 12 to hit a different location on the anode, thereby causing the x-ray beam to be emitted from a different emitting location 16.

In one configuration, shown in FIG. 20, a changing magnetic field generated by, for example, a solenoid coil 212 attached to the housing of the x-ray tube 210, deflects the x-ray beam. The energized coil 212 produces a magnetic field and an associated Lorentz force on the electron beam in the x-ray tube 210, shifting the impact spot on the anode target 214 from which x-rays are emitted. The emitting location 16 moves due to the displacement of the focal spot of the cone beam on the anode 214. The result is that the emitting location 16 moves from one location to another. Careful control of the coil 212 can produce movement in as small as a one-pixel pitch in one or two dimensions.

In another configuration, the electron beam is deflected as it passes through charged metal plates. The direction of deflection depends on the polarity and amount of charge of the plates.

In another configuration, a light source such as a light-emitting diode (LED) or laser are used as the source to generate the electron beam, which is then amplified by a multiplier tube. A light deflector such as optics or mirrors, and acoustic optical deflectors are used to deflect the light. An ultrafast laser may be used to generate an ultraviolet emitter that emits ultraviolet light, a photocathode operably coupled to the ultraviolet light-emitting diode that emits electrons, an electron multiplier operably coupled to the photocathode that multiplies incident electrons, and an anode operably coupled to the electron multiplier that is configured to produce X-rays. The ultraviolet emitter may be steered at different angles to control the output of the electron beam which, in turn, changes the direction or the location of the x-ray beam emitted from the anode.

In another configuration, irradiating arrays of metal components, such as nanowires, with intense femtosecond laser pulses produces high-brightness picosecond X-ray pulses. The emitting location 16 can be moved by using optical steering devices to change the impact location of the laser beam on the metal components.

Multiple photocathodes or a multiplier may be used to collect the steered laser beam and output an electron beam. In some instances, the electron beam may be steered quickly via electronic, magnetic, optical, and/or crystal plus ultrasound, or other means. One way to do this is to use a 2D array of collimators, the holes being integer multiples of a pixel pitch apart, raster scan x-ray beam using different mechanisms including magnetic means.

In another configuration, the x-ray source comprises micron-scale metal x-ray emitters which can be modulated and switch on and off to control the emitting location.

In another configuration described in U.S. Patent Publication No. 2010/0189223A1, the x-ray source 12 is a digitally-addressed flat panel of x-ray sources, where one or more emitters are located in each pixel on a 2D flat panel.

In another configuration, ultrasound can modulate an x-ray beam in space and time. For example, space-time modulation of an x-ray beam is done by total external reflection on a YZ-cut of a LiNbO/sub 3/crystal modulated by surface acoustic waves. The x-ray diffraction is determined by the amplitude and wavelength of the surface acoustic waves. An x-ray beam is aimed at the crystal and the crystal dynamically steers the beam depending on how the diffraction properties of the crystal are changed by the modulating acoustic wave. The output location of the x-ray from the crystal may be varied. For example, the x-ray beam may be modulated to exit from crystal at various locations on an XY plane.

In another configuration, relativistic electron beams with current modulations at a nanometer scale and below may be used to generate coherent x-rays. The current modulation is produced by diffracting relativistic electrons in a perfect silicon crystal, accelerating the diffracted beam and imaging the crystal structure, then transferring the image into the temporal dimension via emittance exchange. The modulation period can be tuned by adjusting electron optics after diffraction. The tunable longitudinal modulation can have a period as short as a few angstroms, enabling production of coherent hard x-rays from a device based on inverse Compton scattering with total length of a few meters.

The spatial position of electron beam where the electron beam strikes the anode, may be modulated by steering the position of the laser beam from the laser pump, which gives rise to the varied position of x-ray emitting position. The present disclosure also contemplates the use of combined imaging systems, for example, interferogram, partially-coherent and coherent x-ray imaging systems. For example systems used in phase contrast imaging methods, coherent x-ray imaging or interferogram based systems upstream of the detector are modified to achieve varied x-ray emitting locations or to generate varied x-ray sources. For example, source grating, where the x-ray is split into multiple sources upstream of an x-ray interferometer, may be used in the generation of x-ray emitting positions. This may be done either by a tunable grid where selected x-ray emitting locations are blocked temporally by x-ray absorbing regions. Such a tunable grid system can be designed into the source grating hardware or can be separate. Another embodiment is that, downstream from the source, the x-ray emitting locations are varied either by using a blocking mechanism similar to that at the source or by moving or modifying any hardware downstream from the source, anywhere between the source and detector, to achieve the end purpose of measurements of regions of interest using varied illumination paths of the region of interest at different times. For example, G1 and G2 gratings may be modified.

Another embodiment of x-ray interferometer is crystal interferometer, or interferometer based on crystal elements.

Figure 21:
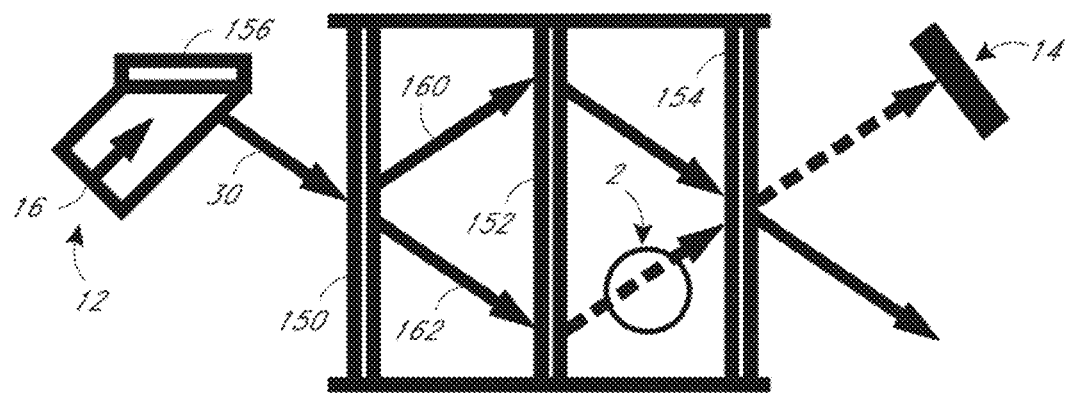
FIG. 21 is a schematic diagram of a system using crystal interferometry.

As shown in FIG. 21, an example of crystal interferometry or x-ray interferometry based on crystals, consists of three beam splitters 150, 152, 154 in a Laue geometry aligned parallel to each other. The incident beam 30 from the x-ray source 12, which usually is collimated and filtered by a monochromator (Bragg crystal) 156 before, is split at the first crystal 150 by Laue diffraction into two coherent beams, a reference beam 160 which remains undisturbed and a beam 162 passing through the subject 2. The second crystal 152 acts as a transmission mirror and causes the beams 160, 162 to converge towards each other. The two beams 160, 162 meet at the plane of the third crystal 154, which is sometimes called the analyzer crystal, and create an interference pattern, the form of which depends on the optical path difference between the two beams 160, 162 caused by the subject 2. This interference pattern is detected by an x-ray detector 14 behind the analyzer crystal 154.

By moving one of the hardware elements, for example, the Bragg crystal 156, the x-ray emitting location 16, or the subject 2, and recording projections from different illumination path using methods described above, the 3D distribution of the refractive index and thus tomographic images of the subject can be retrieved.

In contrast to the methods below, with the crystal interferometer the phase itself is measured and not any spatial alteration of it. To retrieve the phase shift out of the interference patterns, a technique called phase-stepping or fringe scanning is used. A phase shifter (with the shape of a wedge) is introduced into the reference beam. The phase shifter creates straight interference fringes with regular intervals, so called carrier fringes. When the subject is placed in the other beam, the carrier fringes are displaced. The phase shift caused by the subject corresponds to the displacement of the carrier fringes. Several interference patterns are recorded for different shifts of the reference beam 160 and by analyzing them the phase information modulo a can be extracted. This ambiguity of the phase is called the phase wrapping effect and can be removed by so-called "phase unwrapping techniques". These techniques can be used when the signal-to-noise ratio of the image is sufficiently high and phase variation is not too abrupt.

As an alternative to the fringe scanning method, the Fourier-transform method can be used to extract the phase shift information with only one interferogram, thus shortening the exposure time, but this has the disadvantage of limiting the spatial resolution by the spacing of the carrier fringes.

"Coherence-contrast x-ray imaging" is another embodiment of interferogram, instead of the phase shift the change of the degree of coherence caused by the subject is relevant for the contrast of the image.

Alternatively the Laue crystals can be replaced by Bragg crystals, so that the beam does not pass through the crystal but is reflected on the surface.

In some cases, two crystals instead of one are used to enlarge the field of view.

It is to be noted that in most, if not all phase contrast measurements and interferometry methods, the amplitude of the x-ray input beam or intensity of the x-ray input beam may be modulated for some measurements.

The crystal-based interferogram or analyzer where the location of the beam splitter can be steered using modulation by ultrasound, or other energy or electronic methods. For example, a liquid crystal based crystal analyzer can be used to adjust the beam splitting locations to generate different illumination paths.

The present disclosure can be implemented in a portable format. For example, handheld, carry on version. Another example of the present disclosure in a portable version is a foldable system which adapted for field inspection or diagnostics or image guidance or material characterization.

Additional Advanced Hardware

It is one aspect of the present disclosure to include the use of a Micro Electronic Mirror (MEM) device for use as 1) a static or dynamic or tunable diffraction grating, in interferometer, or as 2) primary modulator for generate high spatial frequency x-ray beams, or as 3) collimator by adjusting critical angle for the incident x-ray beam.

a crystal or liquid crystal based device for use as 1) a static or dynamic or tunable diffraction grating, in interferometer, or as 2) primary modulator for generate high spatial frequency x-ray beams to separate scatter and primary x-rays, or as 3) collimator by adjusting critical angle for the incident x-ray beam.

Methods

An element of the present disclosure includes methods of rapid, high-resolution 3D image reconstruction of a region of interest in a subject by moving the position of the x-ray source emitting location relative to the detector in smallest possible increments, for example, pixel increments to only a small number of positions in the area of approximately n2 in the XY plane to acquire the image data necessary for resolving n2 unknown pixels along the Z axis. Where n is the highest unit number in the x or y axis describing the x ray emitting location in a 2 D plane. This allows for a system that requires fewer 2D projection images, less motion requirements, or less motion movement, or a combination of these elements, which means less time needed and less radiation exposure to reconstruct multidimensional images than in the prior art.

In an x ray measurement using a 2D detector, the unit measurement of n maybe that of a pixel pitch of the detector.

In some cases, the relative position of x ray emitting locations adjacent to each other maybe less than one pixel pitch, but still produce measurements for the project path which may be used to resolve the unknown voxels in the z axis perpendicular to detector.

In some cases, such as in an x ray microscopy device, the resolution of the camera, therefore the pixel pitch, maybe much larger than the measurement unit or the resolution achieved in the subject. For example, in the nanometer or sub nanometer range. As a result, the measurement unit of n or the distance between adjacent x ray emitting positions maybe in the range of resolution to be achieved in the subject, for example, sub-nanometer or single digital nanometern, or as small as the achievable resolution allows. This means that instead of a measurement of a pixel pitch for the distances between adjacent x ray emitting positions, the distance may be many times smaller than a pixel pitch of the light camera. In some in cases, as small as the smallest x ray wavelengths, for example, 0.01 nm.

The present disclosure also describes methods where the subject moves relative to the x ray source and detector, such as a part on an assembly line. The x ray 3D measurements maybe done by calibrating and registering the x ray emitting positions, the element of detector, relative to the location of the part, as the part moves through the assembly line. 3D image acquisition maybe achieved independent of the unknown volume introduced by the movement of the part. The movement of the part may also be used as part of measurements done to resolve unknown voxels along the z axis. the number and locations of the x ray emitting position can be determined based on a similar strategy. The goal is to minimize the total area of the movement and to minimize the movement distance so that the depth or the z axis of a new unknown volume introduced in the process of resolving the unknown voxels of the region of interest is minimized.

The methods include the following elements:

Determine the number of 2D images needed for reconstruction of the desired 3D images.

For example, if the 2D detector array has m×n detector cells, then any number p of 2D images, where p<n and p<m, and p is the third axis unknown variable, >3. This results in p number of 2D images with m×n pixels each.

Figure 22:
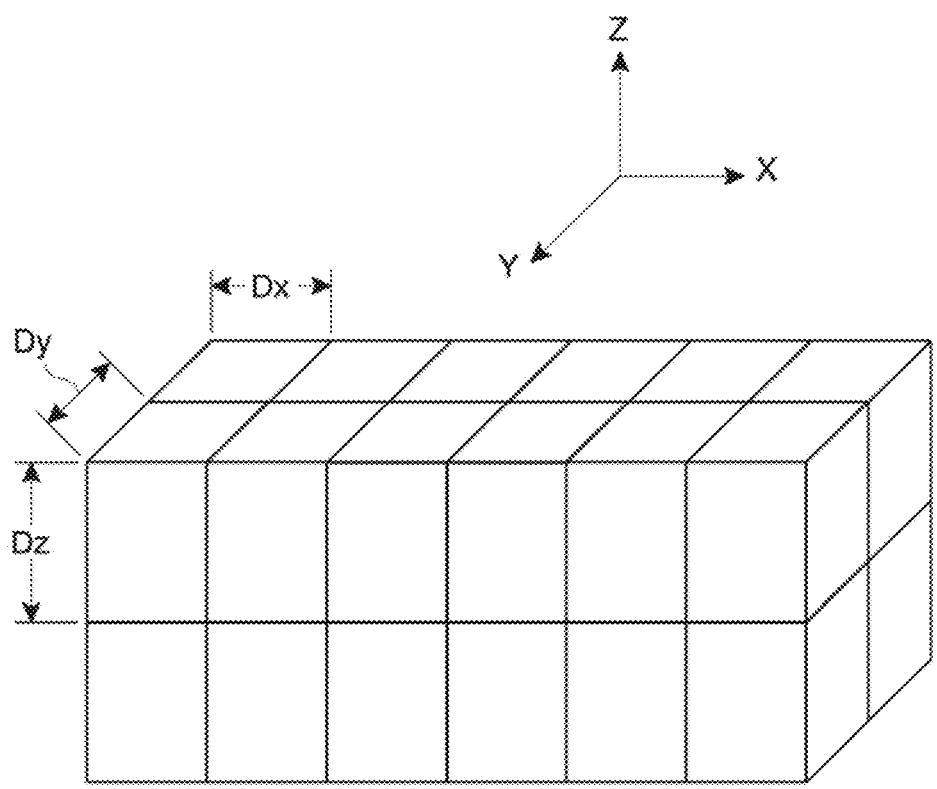
FIG. 22 is a schematic representation of voxels as assumed by the present disclosure, where $D_x = D_y \neq D_z$.

The basic method is to solve a linear equation system with m X n X p variables and m×n×p equations. Current methods do not assume that each voxel in the region of interest of the subject is cubic, that is, the sides of each voxel are the same length, $D_x=D_y=D_z$. The current methods apply to the case where the side in $D_z$ is not equal to $D_x$ and $D_y$, shown schematically in FIG. 22.

When the location of the x-ray emission position 16 relative to the detector is shifted one pixel pitch in the x or y direction parallel to the detector, the new emitting position can generate x-ray beams to illuminate the region of interest with different projected paths than the previous position. This means that, in each projected path, there will be voxels with different spatial position within m×n×p m,n,p) in the projected path, which leads to different x-ray measurement position on the detector.

When such positions (i,j) on the detectors are correlated to the x-ray emission position 16 which is the spot on source 12, illustrated in FIG. 1, FIG. 14, and FIG. 15, as the subject is placed in the illumination path, different locations on the detector measures attenuated signals x of the projected path signals within the volume of the region of the interest, each measurements is correlated to the relative position of the x-ray source and the detector as determined by previous derived geometric information. where each projected path is comprised of P voxels, each containing its specific attenuation coefficient.

In a volume of m×n×p where p is the third axis thickness or variable, in the region of interest. Varying different x-ray source emission positions p times, different 2D projection images are generated so that each pixel on the detector measuring projected line signals from the region of interest contain unique set of pixels with fixed spatial relationship between the pixel elements. Each 2D image is comprising at least m×n measurements, are measured p times, thereby creating m×n×p known measurements. The dataset is then used to resolve unknown voxels in the m×n×p space which are variables responsible for generating varied x-ray measurements at corresponding locations on the detector at varied x-ray emitting positions.

In cases, where the unknown pixels of the subject are embedded in the volume of known pixels of the subject, the x-ray emitting positions may be shifted by a fraction of the pixel pitch to resolve the unknown pixels by creating projection paths sampling at finer steps, so that the projected paths include at least one unknown pixel and, but at the same time do not introduce new unknown pixels.

In addition, in cases where the resolution requirement is not as high as the detector pixel size, it is within the present disclosure to define the resolution required and the corresponding measurement resolution. For example, if the resolution required is 500 μm and each pixel on the detector has a pixel pitch of 100 μm, it is one aspect of the present disclosure to move the x-ray emission location at 500 μm. When the 3D image acquired at 500 μm resolution is obtained for the region of interest, further measurement at finer steps, for example 100 μm, may be used to resolve finer details in the selected areas within the region of interest.

Furthermore, in situations where the material composition is determined and anatomical markers and dimensions are derived either using multiple-energy material decomposition or using lower resolution 3D imaging method, or is simply given, or derived based on known facts, such information can be used to select one or more regions for further finer resolution imaging.

The following general steps can be performed to determine a 3D image: (1) Calibration; (2) 2D imaging; (3) 2D image scatter removal; (4) 2D functional imaging; (5) 3D/multidimensional image calculation; (6) 3D/multidimensional functional imaging; and (7) 3D/synthesized 2D/multidimensional image presentation Each step is optional and the steps can be performed in a different order.

Calibration

Before performing an image acquisition of the subject, a preliminary geometric relationships can be determined for each x-ray source location and the detector without a subject. As illustrated in FIG. 30, A subpixel or pixel transmission can be calculated for each cell (i,j) on the detector 22, where i,j denotes the pixel or region x,y position on the detector 22 where it receives the x-ray signal passing through voxels on the projected path, 1, 2, 3, . . . 11, 12, etc. The pixel pitch is the distance between the x-ray source movement steps or the distance between adjacent x-ray emitting positions. Xa, the pixel pitch of the detector, may be the same as Xc, which is the resolution or the unit of measurement in depth or in the axis perpendicular to the detector. In some instances, Xa may be smaller than Xc, the resolution required in the Z axis, Xc. X ray emission positions move in Xc increments in order to achieve the required resolution.

The basic method is to solve linear equation systems with m×n×p variables, and m×n×p equations. Current CT methods assume that the pixel has a size Xa=Xb=Xc, the present disclosure however extends to the case where Xc is not equal to Xc. When looking at the x ray as it passes the pixels, current methods take the value 1 or 0, 1 for the ray passing through the pixel, 0 if not. In the present disclosure, before conducting acquisition of the region of interest, a registration is made at each angle and x ray emitting position (i,j) receives a signal passing through 1, 2, . . . 12, each subpixel transmission can be calculated. Assuming that inside each pixel, the transmission is uniform and proportion to the volume.

This geometric calculation can be done in advance and stored in the computer. Alternatively, a general formula can be derived for how to write the equation system in numerical format.

Starting with the equation system m×n×p equations, with m×n×p variables, for each direction of projection x ray source or x ray emitting position, there are m×n projection data points, recorded by the m X n detector cells. Each equation has m×n×p variables, there are (m×n)×p equations, thus the linear equation system should be solvable by either iterative method or matrix method.

In one preferred embodiment, if a subject of certain dimensions is to be imaged, the thickness or dimension measurement in the Z direction for the region of interest can be provided ahead of the time. This can be done by
 1. a user input, or
 2. data derived from, for example, mechanical measurement tools or
 3. by 2D x ray measurements at multiple energies to determine the thickness based on a database established using previous measured data of the same or similar materials, or
 4. by simulated data, combined with one or more 2D images at single energy or dual or more energy
 5. x ray measurements at two or more different emitting locations, or
 6. by one or more non-radiation sensor.

In addition, the location of region of interest, relative to the x ray source and detector maybe determined using the techniques as described in 1-6.

For example, a component size of 2 cm in xyz dimensions labeled with contrast agents, or a region of interest in the bone and its immediate region for arthritis identification, a strained stress region of the bone or certain area of a semiconductor assembly line, an area of interest in a luggage for security inspection, a region of interest for detailed inspection of a part in an assembly line.

Based on the resolution Xc as illustrated in FIG. 30 required, then the number and location of x-ray emitting positions are determined for 3D imaging of the subject. Prior to illuminating the subject from different x-ray emitting locations, calculations or calculation and measurements may be performed to correlate the relative x-ray source locations and pixel locations on the detector for their corresponding projected paths within the volume where the region of interest in the subject is placed. Therefore, each projected path in 3D dimensions of the region of interest is related to the x-ray source location and pixels or pixel regions on the detector, where such projected x-ray signal is measured.

After the 2D images are taken, solve for the equation system m×n×p equations with m×n×p variables. Each emitting location of the x-ray source produces an image of size m×n. And each element of the detector receives x ray transmitted through a predetermined projection path, some of the elements receives x ray transmitted after attenuation at the region of interest in a 3D space. There are a total of p third axis variables or unknown pixels that need to be resolved to provide the complete 3D image of the region of interest. For example the total attenuation variable Attenuation $X_{total}$ along any given projected path with the total number of pixel numbers being Z is $$X_{total}=X_1+X_2\ldots+X_z \qquad (3)$$

As illustrated in FIG. 30. Each X out of the $$X_1, X_2 \ldots X_z$$

Corresponds to a unique subpixel or pixel in the m×n×p volume in the region of interest.

There is an issue of completeness, for example, when the unknown pixels outside of the region of interest are introduced into the measurements as the relative position of the x-ray source and the detector moves. There are three situations. (a) When the region of interest of the subject is well inside the imaging area, completeness of the 3D image is assumed because the linear equation system usually gives the right solution. (b) When the region of interest extends beyond the imaging area in one dimension, there is an issue that will be discussed below. (c) When the region of interest extends beyond the imaging area in two dimensions, there is also an issue further discussed below.

Figure 16:
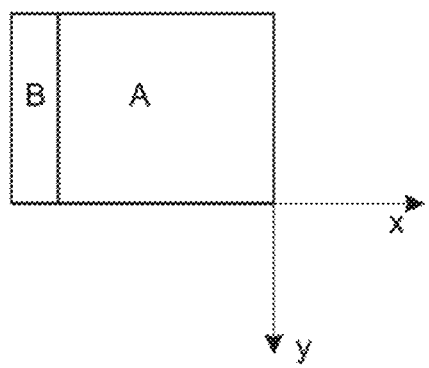
FIG. 16 illustrate unknown regions

Assume that region A is the region of the interest and region B is adjacent to region A. But for acquiring projection data of the region A, we must deal with the data in the region B. Region A is surrounded by region B by conducting a two-step imaging process in which x-ray sources are moved differently, or a two-step scan if x-ray emitting positions are moved differently due to the electron beam being steered to scan anode target at various locations. This generates x-ray at different locations. Information in the region B can be accurately gained without further extending to a larger region. The method of the present disclosure allows for minimizing x-ray measurements required for reconstructing the multidimensional image. For example, using a two-direction move, or raster scan in 2D area, acquire projection images along the X direction and the Y direction, NX data points and NY data points, total projections on the 2D plane, is (NAX+NBX)(NAY+NBY) as illustrated in FIG. 16.

Region A has NAX×NAY pixels
Region B has NBX×NBY pixels
Total (NAX+NBX)(NAY+NBY)pixels=NAX×NAY+ NAX×NBY+NAY×NBX+NBX×NBY, new unknown NAX×NBY+NAY×NBX For example, the region of interest A has an X dimension of 20 cm, a Y dimension of 20 cm, and a Z dimension of 20 cm. If the pixel pitch of the x-ray detector is 200 µm, there would be 1000 data points. In other words, there would be 1000 unknown data points to be resolved. Therefore, when the x-ray from the source is scanned in the XY plane parallel to the detector, x-ray images are sampled by at least 1000 different emitting positions. The distance between each of the adjacent emitting positions can be chosen to produce the minimum number of unknowns and, at the same time, minimize the sampling time.

For example, steering the x ray emitting position along the x axis and y axis at 1000 first positions within an area of 33×33, acquiring measurements at each position, and the distance between adjacent emitting positions is the pixel pitch of the detector, which is 200 µm, However as the x-ray emitting position changes to illuminate region A, unknown pixels in region B, the area surrounding region A are introduced The solution to the above problem is to make the scan step finer in a second position, so that all the information in region B can be accurately gained without further extending to an even larger region.

Figure 17:
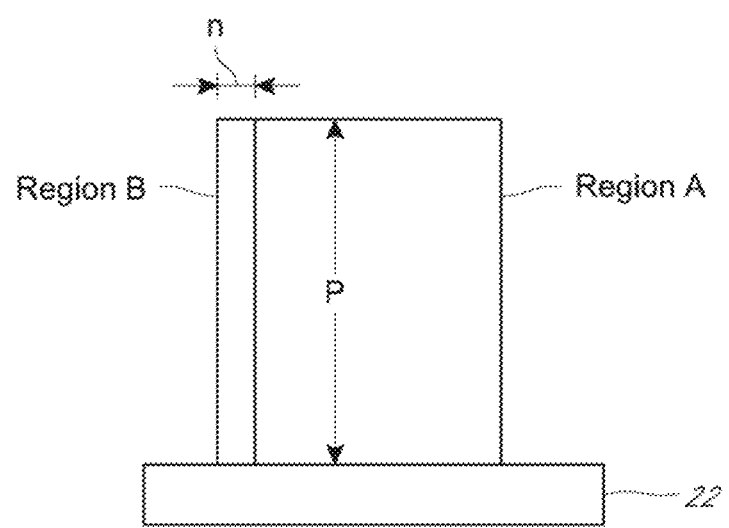
FIG. 17 illustrates an embodiment of resolving for the unknowns in the z axis.

The scanning of x-ray source or the x-ray emitting position remains in the scanned area in first position, except now, the x-ray source is scanned in finer steps which illuminate x ray on the region of interest and unknowns in Region B. For example x rays can be sampled a fraction of movement step size, or a fraction of pixel pitch, from a previous x-ray emitting position. If each emitting position is different from the previous emitting positions in the step described earlier, however at the same time, are only illuminating the unknown pixels which need to be resolved within Region A and Region B, additional measurements which may lead to formulation of new linear equations which reveal new relationships between existing unknowns in the region of interest Region A or subsets of unknowns of Region A and those newly introduced in Region B outside of region of interest in the step described earlier. The sets of linear equations may be derived to give rise to the complete solution as illustrated by equation (3), where each of the pixel in the projected path comprising a unique set of pixel or voxels in the region of interest A and in some parts outside of region A. The newly introduced unknown regions will have a depth or measurement in the z axis such as $p=n^2$ as in FIG. 17 and the total volume of new unknowns introduced is $4 \,n \times n^2$, $n^2$ being the depth of the region of the interest, the unit of measurement is the movement resolution or movement steps. For example, if there are 100 unknowns along the z axis in region A, the total unknowns introduced newly is 4×10×100 if the x ray emitting positions have moved within 10×10 area in the XY plane. If however the x ray emitting position moves in a larger area, for example, 15×15, then the furthest area from the original position will be higher, as a result, new unknowns introduced will be a lot more, the total unknown is now 100+4×15=160. 15×15 more than needed.

When the depth is $n^2$ 1000, xy direction move is square root of 1000, which is approximately 32, newly introduced unknown is 4×32=130 and the total unknowns is 1130, or approximately 34 or in order to resolve the 1000 unknowns in the z axis, ideally x ray emitting positions will be at 1130 different first positions, each would be pixel pitch apart from its most adjacent spots, the x ray emitting positions is less than 34 or approximately 32 pixel pitch away from the original position in the x direction and the y direction in order to minimize the imaging time.

For the step of finer scan, second points, the x ray emitting position can have a different center point than the first positions and/or have a fraction of a pixel pitch movement increment. And this step maybe combined with the earlier step by predetermining which one or more regions of the XY area, movement increment size. These regions then have higher density of spots of x ray emission positions. The order of movement, to the first positions or to the second positions, in some applications, is not critical, and may be done in one scan as they may be interwoven in the selected area.

The present disclosure also provides methods in which, independent of 3D imaging measurements, if the relative spatial position of the region of interest, or the subject to the x ray source changes in any 6D dimension (for example by the movement or the rotation of the region of interest or by movement or the rotation of the x ray source) the system can use the movement to resolve a 3D image. Because of the movement in 6D, elements of the detector will correspond to a different projected path in the region of interest. The movement may be divided in increments of at least one measurement unit with different x ray measurements for each spatial position of the subject during the movement. The geometry of the movement relative to the x ray source and detector may be calibrated spatially. Each projected path detected by a corresponding detector element or pixel or element region of the detector with two or more pixels may serve as a data point in solving for the unknown pixels or voxels in the Z axis for the region of interest. The newly introduced unknowns because of the movements will be determined on a case by case basis.

A system where the x ray emitting position is moved in an xy plane parallel to the detector may be combined with the above x ray measurements during such movement.

Such 3D imaging method is fast and simplified.

However when such a system is not available, in one configuration of this disclosure to include multiple dimension tomography known to those familiar to the art as an alternative step to the 3D imaging method described here as part of the present disclosure to improve other alternative 3D tomography systems based on 2D detectors.

2D Imaging

Multidimensional images are generated from 2D images taken from at least two different x-ray emitting locations. The following provides one example procedure for determining the 2D images using an x-ray machine.

A determination of the geometry and dimensions of the subject or the region of interest in the subject can be determined. If such information is predetermined or preset, this step can be skipped.

The subject is then illuminated with x-rays from a first x-ray emitting location. The image is then read at the detector assembly.

Next, move the x-ray emitting location to a second location in the XY plane parallel to the plane of the detector assembly, where the displacement from the first location to the second location is an integer multiple of the detector pixel pitch. When the displacement is one pixel pitch, a projected image of the region of interest of the subject differs from the previous projected image by extending the outer edge of the image of the region of interest by exactly one line of pixels on the detector assembly along the axis of the change of direction. In another words, moving the x-ray source or emitting location generates two different projected images for a region of interest of defined dimensions, and the location of the projected images on the detector for the same region of interest is only extended by one pixel pitch in the direction of shift.

Repeat the x-ray emitting location step and measurement step.

Alternatively, there are various ways to generate projected images on the detector with the end goal of minimizing new unknown pixels outside of the region of interest in the projected paths in the 3D imaging process. For example, the x-ray source emitting position may be modified to move in 3D space or in at least one dimension. As long as a certain aspect or a portion of imaging process, if not the complete imaging process, use the present method, the imaging methods of the prior art may be improved. Alternatively, in cases where the subject or the region of interest moves, for example, in a conveyer belt, or a moving component in the region of interest, such as tracking an unknown component inside a cavity, the movements varies illumination paths of the component and at the same time generate the new unknown pixels in the illuminating paths of the component. Such movements alone may be sufficient to complete a 3D imaging dataset. In some cases, in order to complete 3D imaging, the relative position of the x-ray emitting position or x-ray source may still need to be moved in order to complete the 3D illumination and imaging dataset. The number of unknown pixels may be increased or varied. However, as long as the illumination paths are varied enough to resolve the complete 3D volume in the region of interest and newly introduced unknown pixels, complete 3D imaging can be accomplished. Repeat the x-ray measurements with as different locations of the x-ray source as needed in order to produce a 3D image of the desired resolution in the Z axis.

Primary X-Rays and Scatter Separation

In this step, scatter is separated from the primary x-rays for each of the 2D images acquired above. A number of different scatter removal or scatter and primary separation methods are described as above.

The present disclosure includes preferred methods of scatter and primary x ray separation where multiple x-ray energy sources are used, and scatter and primary x-rays are separated at each energy level, methods and details of material decomposition can be found in PCT application PCT/US19/14391, which is incorporated herein in its entirety.

The configuration of adjustable beam selectors in FIGS. 4-15, FIG. 8, and FIG. 9 are used in applications where the movement or x ray emission source or the emitting location of the x ray moves out of the alignment of holes in the beam selector for the primary x ray to pass through, the beam selector means are either insensitive to the x ray emission position, can remain aligned or can be adjusted to align again with the x ray source as described above in between 2D x ray image acquisition on a per need basis.

2D Functional Imaging

Although functional imaging is described above as an optional independent step, it actually is performed as modifications to the 2D imaging. Functional imaging is providing information in addition to location or 2D visualization taken with a single-energy x-ray source with or without scatter and primary x-ray separation. Examples of functional imaging methods and systems are described below. Each example is independent of the others and may be combined to provide more information as needed for applications.

Material Decomposition and Different Material Imaging

This method can be done for 2D images or after reconstructed multidimensional images or reconstructed 3D images. For example, material decomposition can be done on measured projected 2D or synthesized 2D or multidimensional images, or 3D images at dual- or multiple-energy or sometimes single levels.

Decomposition is the process by which dual- or multiple-energy x-rays are used to quantitatively analyze and separate components in the subject based on atomic z and density or other x ray sensitive characteristics of component in the region of interest.

In one configuration, the x-ray source emits two x-ray pulses from each x-ray source location: a high-energy pulse at an average energy level H, followed by a low-energy pulse at an average energy level L. In another configuration, the x-ray source emits three x-ray pulses from each x-ray source location: a high-energy pulse at an average energy level H, followed by a medium-energy pulse at an average energy level M, followed by a low-energy pulse at an average energy level L. In each configuration, each pulse has a single, essentially unchanging energy spectrum. In another configuration, four or more energy pulses are emitted from the x-ray source.

In one configuration, rather than the 2D detectors described above that cannot discriminate between different energy levels, the detector assembly employs energy-sensitive, photon-counting detectors. These detectors may be used with a conventional x-ray source, or with a time of flight x-ray source, such as a picosecond x-ray source, to collect primary x-rays for densitometry and quantitative analysis and separation of images for different components with varied atomic z. With a conventional x-ray source, the energy-sensitive photon-counting detector replaces the front detector, rear detector, or both in the dual-detector plus beam selector assembly to ensure primary x-ray and scatter separation, while at the same time, allowing dual-, triple-, or multiple-energy and spectrum-energy imaging and spectroscopy of different materials or components in the subject.

Details of material decomposition using dual or multiple energy sources can be found in PCT application PCT/US19/14391, which is incorporated herein in its entirety.

The present disclosure also provides methods in which single energy x ray measurements are used for material decomposition. The method can have the following optional elements:

conducts multiple dimension or 3D X ray imaging of the region of interest;

such images are of primary x ray image with scatter reduced to less than 1% of the primary signal, or in some cases less than 5% or in some cases, less than 10%;

determines one or more estimated material characteristics, such as atomic number and density, spatial position, and other characteristics which are defined by temporal marker or anatomic marker, or one of a marker defined by facts deduced from digital analytical algorithms performed on data derived from multiple sources of the same or similar region of interest in the same or similar subjects;

for systems with multiple measurement units in the region of interest, using a tomographic reconstruction method described in the present disclosure (these estimated material characteristics can then be modified by reference to stored known material characteristic data);

determining the composition of the volume in the region of interest during reconstruction includes segmenting one or more regions of interest into components, each with a common composition;

the segmenting can be performed during iterative reconstruction instead of being based on the voxel characteristics determined upon the completion of iterative reconstruction;

one or more additional iterations of the tomographic reconstruction algorithm, where each iteration updates the one or more estimated material characteristics for components in the region of interest.

Functional imaging is improved when primary x-rays and scatter are separated.

Material Separation and Imaging

Interferometry

In one configuration, an interferometer is employed with or without scatter removal. With this, 2D images of absorption, dark field, and/or phase contrast images can all be obtained. Such images are used to construct a 3D interferogram.

The interferometer operates by emitting x-rays through a phase grating that introduces an interference fringe at specific distances downstream. When a subject is placed in the beam's path, the subject modifies the observed interference pattern via absorption, refraction, and small-angle scattering. Once these signals are read by the detector, the properties of the subject and its components can be determined algorithmically. In one example, Talbot-Lau interferometry is used in order to have a large field of view. In Talbot Lau interferometry, a beam splitter grating (G1) is placed in the beam path between an x-ray source (S) and detector (D). Due to the fractional Talbot effect, an intensity distribution (I) revealing the periodic structure of the beam splitter grating occurs at certain distances behind the grating. If an object (O) is placed in front of the beam splitter grating, the intensity distribution changes due to the absorbing, scattering, and refractive characteristics of the object. The fractional Talbot effect requires spatially coherent radiation. To meet this requirement, a microfocus x-ray tube with a sufficiently small focal spot can be used. Alternatively, a slit mask (G0) can be placed in front of the focal spot of a conventional x-ray tube. The mask absorbs certain parts of the x-ray beam and thereby creates spatially coherent slit sources. Each of these slit sources generates a self-image of the beam splitter grating. By exploiting the Lau effect, it is ensured that these self-images superimpose to a sharp intensity distribution. In general, these interference fringes are too small to be resolved by a conventional x-ray detector. To overcome this challenge, an absorbing analyzer grating (G2) with the same period as the interference fringes is placed at the plane of these fringes. This analyzer grating is used to sample the periodic intensity distribution by shifting it stepwise in its plane perpendicular to its grating bars.

In order to generate coherent x-ray beams, for example, the interferometer uses a pixilated x-ray source or coherent source grating. In another example, the interferometer has a diffraction grating, which is MEM-based, crystal-based, or employs an acoustic modulated crystal grating.

3D Imaging

High-resolution 3D imaging of a subject with defined dimensions, has the following steps.

Calibration is as described above.

Primary x-ray and scatter separation and/or functional imaging. Examples are as described in U.S. Provisional Patent Application Nos. 62/620,158, 62/628,370, and 62/628,351, as explained above, dual- and multiple-energy imaging.

The x-ray emitting location shifts relative to the subject to a second position in an x-ray plane parallel to the plane of the detector. The shift distance between the x-ray emitting positions is set so that each subsequent image contains a projected image of the region of interest whose location differs from the previous image by extending the outer edge of the detected image for the region of interest by one line of pixels on the detector, and along the axis of shifting direction. Repeat the x-ray measurements for each x-ray emitting location. The locations can also be shifted by less than one line of pixels, or by more than one line of pixels.

Determine the geometry or the dimensions of region of interest in the subject. If such information is predetermined and stored in the computing device, skip this step.

Based on the thickness in the Z axis perpendicular to the x-ray plane, determine the total number of pixel-wide x-ray-emitting locations P needed in order to produce a complete 3D image, wherein P=thickness/pixel pitch (or resolution needed for the z axis)=$n^2+4n$. If such information is predetermined, skip this step.

Repeat moving the x-ray emitting positions to the first positions and x-ray measurement at least P times in the XY plane with the emitting positions in a travel area limited by coordinates on the x- or y-axis: smaller or equal to $\sqrt{(n^2+4n)}$. In cases when 4n is sufficiently small compared to P, p-4n first positions are sufficient for 3d imaging reconstruction. To resolve unknowns introduced in the new x ray emission position, second position are scanned. This is when x ray emission positions are closer in distance to adjacent second positions than those of adjacent first positions, but travel in the same area as the first positions.

It is noted that for x ray with pixilation x ray source, instead of moving the x ray source or physically moving x ray emission position, different pixels are used as the x ray source, each time an image is taken.

Combine x-ray measurements as described above, solve and determine the unknown pixels in the Z axis for the region of interest in a linear equation system m×n×p. Solve for and determine the new unknown pixels created from all x-ray emitting locations other than the first location.

The computing device uses a conventional computing tomography imaging algorithm, including simply plugging in the resolved unknown pixel values to derive a 3D image of the region of interest base on the previous steps. The computing device provides a multiple-axis representation at various resolutions of 2D images combined with a multidimensional representation of both for the region of interest in the subject.

The x-ray emitting location can be moved in planar space less than 5 mm×5 mm, 4 mm×4 mm, 3 mm×3 mm, 2 mm×2 mm, or 1 mm×1 mm to derive complete 3D images of 100 μm resolution of a chest image of 20 cm×20 cm×20 cm. This allows for a significant increase in the speed of measurements and a significant drop in the amount of radiation required to obtain a 3D image. As a result, patient safety and comfort is dramatically increased.

The present disclosure includes embodiments where the x-ray measurements for a subject of 20 cm×20 cm×20 cm to derive a complete 3D image using less than 1150 images or in some instances 1000 images at 100 μm resolution, in some instances, with scatter being <10% or 5% or 1% of the primary x-ray signals. With higher resolution, such as 100 nm or 10 nm, proportionally, the number of x-rays measured will be increased, for example 1 million images. However, for a 10 mm×10 mm×10 mm sample, at 100 nm resolution, there will be 100,000 measurements, or 30 µm×30 µm movement of the x-ray emitting location in the XY plane to derive a complete 3D image.

It is also one aspect of the present disclosure to image large subjects, such as 25 cm×25 cm×25 cm, with small movements in the x and y directions, such as 5 mm or sometimes even less, for example, 1 mm, relative movement of the x-ray emitting locations to the subject is accomplished on a two dimensional plane with resolution or distance between adjacent x ray emitting locations to be in the 100 µm, or 0.1 um depending on the resolution required and achievable resolution, defined by the pixel pitch of the detector hardware. The furthest x ray emitting position from the original position maybe less than 5 degrees, or 4 degrees or 2 degrees or less than 1.5 degrees in order to achieve complete 3D imaging with minimum number of 2d images taken. For lower resolution measurements such as 500 um for a subject with 25 cm in thickness or in depth, the furthest x ray emitting position maybe 7.5 cm from the original position, with significantly less number of images taken than for the higher resolution such as 100 um or 0.1 um in order to complete 3D image reconstruction The present disclosure allows measurements and thereby 3D image construction of a subject in the subnanometer range, such as 0.01 nm or 0.1 nm. For example, for a subject with dimensions in 10 µm×10 µm×10 µm, 10 µm being the thickness, using an x-ray microscopy, the resolution can be in the subnanometer range. An x ray microscope, as illustrated in FIG. 31 (35), which can have a condenser lens m-1, aperture, m-2, objective lens, m-4, and an x-ray detector assembly, m-5. M-5 can be, for example, a x ray detector or photodiode arrays or photon counter, spectrometer comprising an energy dispersive x ray optics such as a grating, and/or a spatially sensitive detector. In some cases, a scintillator to convert the x-ray signal into optical light can use the following to measure the signal: a camera sensor, photon sensitive camera or PMTs or PMT array or The subject can be placed immediately after the aperture. X-rays emitted from an undulator as insertion device in an electron (or positron) storage ring is monochromatized, m-7, and focused onto the sample, m-3 by a condenser, m-1, which can be a zone plate, whereby the objective lens magnifies the signal onto a detector m-5. The sample is raster scanned and the transmitted intensity monitored by a x-ray sensitive detector m-5. The distance between the most adjacent x ray emitting positions can be as small as 0.01 nm to 100 nm depending on the application need. The condenser lens, m-1, can also be a specialized X-ray optics called multilayer Laue lenses (MLLs) which are two perpendicularly oriented lenses. These lenses consist of alternating layers of two different materials with nanometer thickness.

With MLLs, the resolution of a x ray microscope can reach 1 nm. In reality, with the present dis, the limitation of x ray microscopy is the x ray condenser optics, theoretically, the present disclosure enables resolution of along the z axis to be the diffraction limit of the x ray wavelength. However, the present limitation is the x ray optics for focusing x ray into a spot as small as 0.01 nm.

A collimator maybe used to select regions of radiation to reduce radiation on the subject. Or alternatively, an anode target maybe modulated and rotated so that regions on the anode target maybe are selected for x ray generation. In another configuration, electron beam emitting source maybe modified to selectively activate electron emitting unit so that x ray radiation is only generated in selected regions. For example, in a field emitter based x ray source, only selected regions of field emitter are activated. For example if 200 elements of field emitter material, such as nanotubes or nanowires are needed to generate enough electron current for the generation of x ray needed for the application, one or more field emitter element, such as nanotubes, or nanowires, may form a field emitting unit, which can also include a computing apparatus, and maybe be activated independently from one another. For example, each field emitter unit may have a similar number of field emitting elements, such as illustrated in FIG. 24, C7. However, in other configurations, each field emitting regions may have different numbers of field emitting elements than the rest.

Mechanisms for activation of each field emitting unit may be the same or similar to what is known to those familiar with the art. A computer processor will dictate which region to be activated at what time. It is also part of the present disclosure to multiplex activation of two or more independent field emitting regions at different times.

Multiple Dimension or 3D Images

It is also an aspect of the present disclosure to include two or more x-ray emitting locations or two or more x-ray sources for the multidimensional imaging of two or more subjects in a region of interest using the 3D imaging method as described. Each x-ray source or emitting location illuminates a distinct path in the region of interest on its respective subject. Such imaging may be synchronized. Selected region multidimensional imaging may be done at the same time with different x-ray sources or x-ray emitting locations, but not synchronized with each other. This means each x-ray emitting location may be moved to illuminate a different projection path on its designated subject or a different x-ray emitting location in the predetermined emitting location is turned on for subsequent illumination. The result is that separate 2D images are acquired of different subjects in the region of interest either at the same time synchronous or asynchronous or at different times as required by the application.

Alternative to the above process of multiple dimension x-ray imaging measurements and reconstruction, another embodiment of 3D image acquisition and generation is based on a scanning-beam digital x-ray (SBDX). SBDX uses an electromagnetically-scanned electron beam incident upon a large-area transmission style tungsten target. The electron beam is raster scanned over a 2D array of source focal spot positions every $1/15$ of a second. A multi-hole collimator defines a series of narrow overlapping x-ray beams convergent upon a 2D detector. The geometric relationship among the narrow beam projections is constrained by the precise and rigid geometry of the SBDX collimator and the fixed detector position. A typical SBDX system geometry is as follows: Source-detector-distance (SDD)=1500 mm; Source-axis-distance (SAD)=450 mm; Focal spot positions=71×71; Focal spot pitch=2.3×2.3 mm; Native detector array=320×160; Native detector element pitch=0.33 mm; and Detector bin mode=2×2.

SBDX has an inherent tomosynthesis capability due to the use of inverse geometry beam scanning. A live display analogous to conventional fluoroscopy is generated using a GPU-based real-time image reconstructor. Each displayed 2D image frame is generated through a two-stage reconstruction procedure. First, shift-and-add digital tomosynthesis is performed to generate a stack of, for example, 32 single-plane images with, for example, a 5 mm plane spacing. The pixel centers for the stack of tomosynthesis images are defined such that a fixed pixel position (for example, row 100, column 100) in the stack corresponds to an x-ray originating at the detector center. Next, a gradient filtering procedure is applied to each of the single-plane images to identify local regions of high sharpness and contrast. The final 2D "composite" image is then formed by selecting, for each pixel position, the pixel value from the single-plane image with highest contrast and sharpness. Due to the geometry of the tomosynthesis pixel centers and the compositing procedure, the final composite image can be viewed as an inverted "virtual" cone-beam projection of the in-focus objects in the subject volume. A virtual SBDX projection originates at the center of the detector and falls on the source plane. The pitch of the virtual detector elements at the source plane is, for example, 0.23 mm based on the set geometry.

Alternatively, various 3D computation tomography configurations and methods can be utilized. These can include, for example, using a motorized x-ray source to span significant angles, move linearly 1D, 2D, 3D or within 6D space, a pixilated x-ray source, or using methods other than what is described above for 3D reconstruction. These can all be combined with the primary x-ray and scatter separation methods similar to, derivatives of, or the same as described above to achieve the resolution required and quantitative x-ray tomography by separate scatter and primary x-rays so that the scatter is <10% or <5% or <1% of the primary x-ray signals.

In a system involving multidimensional x-ray imaging methods, when scatter is small compared to the primary x-rays, for example in a low-scatter sample or small animal, multidimensional images may be constructed without involving the primary x-ray and scatter separation step.

It is an aspect of the present disclosure to include embodiments of a method comprising of steps:

Deriving a low resolution 3D or 2D image as described above, using more than one pixel or region of pixels as a unit of unknown voxel. Based on an image or images derived above, selecting a subject region to be imaged in higher resolution, for example, as high a resolution as a single pixel. Higher resolutions may also be applied to methods where visible light, optical detectors are used downstream of an x-ray scintillator, converting x-rays to visible light, and captured by the visible light, optical detectors or visible light photodiodes or photodiode array. In this case, the pixel size resolution may be the resolution of the camera or visible light detector or photodiode.

A high-resolution image can be derived as described as above and a low-resolution image of a subject may be derived using methods described above to track the subject. Low-resolution may be defined with a measurement unit of two or several pixels, rather than of one pixel. For example, for a 20-cm-thick subject, at a 5-pixel resolution and each pixel at 100 µm in pixel pitch, each measurement unit is 5×100 µm=500 µm. There would be 20 cm/500 µm=400 unknown units or 400 positions that need to be resolved. So only 20 unit×20 unit area of x-ray emitting locations, or <4 mm×4 mm area where x-ray emitting locations need to be scanned in the XY plane.

Medical applications include, but are not limited to, detecting cardiovascular abnormalities, detecting factures and other musculoskeletal injuries, aiding the diagnose of neurological diseases, dental, screening for cancers, diagnosis of thoracic complications and conditions, surgical and procedure guidance and biopsy guidance, and treatment management and monitoring. Industrial applications include, but are not limited to, x-ray inspection and identification, security, and environmental issues.

It is one aspect of the present disclosure to include the following methods based on the existing hardware configuration due to the fact that the present disclosure enables detection of temporal markers and dynamic events in millisecond or faster in 2D and multiple dimensions and 3D:

Time: time stamp each image taken, either 2D or 3D, or more multiple dimensional, such as attach a DICOM label or adding a time label.

Fluidic dynamics, flow direction, dynamic movement in 6D: by using contrast agents such as x ray measurement sensitive markers, nanoparticle labeled markers or microbubbles administered in one or more phases. The administration maybe for example, oral intake or by injection or inhaling or means known to those familiar with the intake method of in vivo contrast agents. The methods are to track, for example, blood flow, liquid flow in a microfluidics or lab on a chip, tracking of a component such as implant or surgical tool or biopsy probe, or disease markers in regions of the body. 3D images or multiple dimension images or gated x ray measurements are done at discrete times during one or more time intervals of interest, markers maybe located by multiple dimensional imaging or 2D imaging or using spectral or multiple energy x ray decomposition at the region of interest. This is useful when the component to be tracked comprised of one or more regions which maybe be distinguished in x ray measurements from the background, for example, when such regions on the component is at an atomic z significantly different from those materials in its background.

Colocation with other measurement modalities, such as optical spectroscopy, endoscope, optical tomography, ultrasound, electrophysiology, MRI or SPECT, or PET or other x ray based measurements, by identification and/or localization of one or more contrast agents shared by x ray and the modalities, one or more spatial marker or anatomical markers or localization of one or more substances both temporally or spatially. Such devices in some configurations have an intracavity probe, such as a catheter and guide wire. X ray imaging of the present disclosure provides the methods to identify and guide the location of such probe and devices by either using material decomposition method, or by using a probe which has one or more regions that are designed to be visible at designated x ray energy levels. In the event, that different chemical or molecular markers are used, in case of X ray markers or contrast agents are different from those used for other modalities, x ray contrast agents maybe conjugated with contrast agents for other modalities, or the x ray contrast agents may relate to the contrast agents of other modalities spatially.

3D imaging and x ray analysis of components inside of a region of interest using chemical based perturbation, such as a drug or energy perturbation such as ultrasound or electromagnetic waves such as laser or radiofrequency means such as in RF ablation of tissues such as heart or kidney, or varied ultrasound perturbation of capillaries or other tissues, the changes in tissue composition in ablated or affected regions may give different x ray measurements during the energy perturbation. An optical probe or ultrasound probe device or catheter which delivers energy such as RF may be used. Such as probe may have regions of material compositions different from the background, which result in varied x ray measurements. Additional, using 2D functional imaging and or 3D functional imaging methods, including material decomposition methods, such changes may be identified and localized. Databases of markers associated with changes during each phases of perturbation maybe established ahead of time to allow referencing and look up to help diagnosis and identification of stages of perturbation.

Identification of the image or image set: for example, each image is labeled with at least the name and or a description of the subject or the region of interest, or at least a unique identification number or binary identification number, or all of the aforementioned id information.

Recording number of images taken per subject based on DICOM labels or unique identifier for each imaging process or each imaging session or each study or treatment or diagnostic or monitoring or therapeutic planning, or research project or tracking period.

Recording and tally number of images taken and or processed for each x ray system including the computer, the x ray hardware and the software; a memory storage unit, electronically store one or more documents, each has reports or up to date records of number of images taken during a time frame such as a day or a month or a year or since the system has been in use; the report or the document can be accessed by either physically accessing the computer and its associated x ray imaging system or the electronic memory storage unit remotely via internet or intranet or direct physical access for example a memory stick or security key capable of storing and process digital information; a computer is programmed to generate a report based on the document, store electronically, and periodically automatically sends the report to the predetermined recipient via email or hardcopy or other electronic means for example, stored on a server, password protected, accessible for the predetermined recipient who can access by login to access the record by using a password either at the x ray system location, and or at a remote location.

The above describes a Minimized Spatial Variance for between each adjacent image acquired and the total deviation from the original imaging position, Minimized Imaging Acquisition Time, Minimized in Radiation and Complexicity, Radiography based CT (3MR-CT), its variant, Spectral or multiple energy version is described as 3MR-SPECTRAL CT and its variant, functional imaging version is describing as 3MR-F-CT.

Thus it has been shown and described a 3D imaging method. Since certain changes may be made in the present disclosure without departing from the scope of the present disclosure, it is intended that all matter described in the foregoing specification and shown in the accompanying drawings be interpreted as illustrative and not in a limiting sense.

What is claimed is:

1. An x-ray measurement device capable of determining three dimensional x-ray images of a region of interest (ROI) in a subject, the x-ray measurement device comprising:
    an x-ray source, the x-ray source configured to emit x-ray radiation at the ROI, wherein a plurality of projection images are acquired with x-ray radiation emitted from a plurality of different x-ray emitting positions relative to the subject, the number of different x-ray emitting positions being quantitively related to a dimension of the ROI along an axis;
    an x-ray detector comprising a plurality of detector elements arranged in a two dimensional plane that is perpendicular to the axis, opposite the x-ray source, the x-ray detector configured to detect x-ray radiation after attenuation of the x-ray radiation by the ROI of the subject and provide an indication of the detected x-rays; and
    a processor configured to receive the indication of the detected x-rays and reconstruct a three-dimensional x-ray image of the ROI from the detected x-ray radiation.

2. An x-ray measurement device capable of determining three dimensional x-ray images of a region of interest (ROI) in a subject, the x-ray measurement device comprising:
    an x-ray source, the x-ray source configured to emit x-ray radiation at the ROI, wherein a plurality of projection images are acquired with x-ray radiation emitted from a plurality of different x-ray emitting positions relative to the subject, the number of different x-ray emitting positions being determined based on a ratio of a dimension of the ROI along an axis to a resolution of the ROI along the axis;
    an x-ray detector comprising a plurality of detector elements arranged in a two dimensional plane that is perpendicular to the axis, opposite the x-ray source, the x-ray detector configured to detect x-ray radiation after attenuation of the x-ray radiation by the ROI of the subject and provide an indication of the detected x-rays; and
    a processor configured to receive the indication of the detected x-rays and reconstruct a three-dimensional x-ray image of the ROI from the detected x-ray radiation.

* * * * *